(12) United States Patent
Blanford et al.

(10) Patent No.: US 7,627,162 B2
(45) Date of Patent: Dec. 1, 2009

(54) ENHANCED VIDEO METROLOGY TOOL

(75) Inventors: Charles Blanford, Hansville, WA (US);
Dahai Yu, Redmond, WA (US); Barry E. Saylor, Kent, WA (US)

(73) Assignee: Mitutoyo Corporation, Kawasaki-shi (JP)

( * ) Notice: Subject to any disclaimer, the term of this patent is extended or adjusted under 35 U.S.C. 154(b) by 837 days.

(21) Appl. No.: 11/185,561

(22) Filed: Jul. 20, 2005

(65) Prior Publication Data

US 2006/0171580 A1    Aug. 3, 2006

Related U.S. Application Data

(60) Provisional application No. 60/648,956, filed on Jan. 31, 2005.

(51) Int. Cl.
*G06K 9/00* (2006.01)

(52) U.S. Cl. .................. 382/141; 382/152; 382/199; 702/95; 709/204; 709/224; 356/615

(58) Field of Classification Search .............. 382/152, 382/141, 199, 145; 702/95, 159; 709/224, 709/204; 356/615, 241.1; 73/865.8, 105; 348/E5.025, E5.047; 250/559.48
See application file for complete search history.

(56) References Cited

U.S. PATENT DOCUMENTS

| | | | | |
|---|---|---|---|---|
| 6,542,180 | B1 * | 4/2003 | Wasserman et al. | 348/131 |
| 7,003,161 | B2 * | 2/2006 | Tessadro | 382/199 |
| 7,324,682 | B2 * | 1/2008 | Wasserman | 382/145 |
| 7,454,053 | B2 * | 11/2008 | Bryll et al. | 382/152 |
| 2002/0009220 | A1 | 1/2002 | Tanaka | |
| 2002/0057831 | A1 | 5/2002 | Hiroi | |
| 2002/0169586 | A1 | 11/2002 | Rankin | |
| 2003/0095710 | A1 | 5/2003 | Tessadro | |
| 2004/0252879 | A1 | 12/2004 | Tiemeyer | |
| 2005/0008214 | A1 | 1/2005 | Willis | |
| 2005/0031191 | A1 | 2/2005 | Venkatachalam | |
| 2005/0109959 | A1 | 5/2005 | Wasserman et al. | |
| 2005/0213807 | A1 | 9/2005 | Wasserman | |
| 2008/0019683 | A1 * | 1/2008 | Yu et al. | 396/121 |

FOREIGN PATENT DOCUMENTS

EP    1475627 A2    11/2004

OTHER PUBLICATIONS

U.S. Appl. No. 10/978,227, filed Oct. 29, 2004, Bryll.
*QVPAK 3D CNC Vision Measuring Machine Operation Guide*, Version 2.0, Manual No. 4911GB, Series No. 359, Mitutoyo Corporation & Micro Encoder Inc., Kanagawa, Japan, Sep. 1996.

(Continued)

*Primary Examiner*—Sheela C Chawan
(74) *Attorney, Agent, or Firm*—Christensen O'Connor Johnson Kindness PLLC

(57) ABSTRACT

A system and method for tool enhancements are provided which allow users to utilize video tools in a controlled manner. The video tools balance a minimal amount of cursor positioning and "mouse clicks" against a level of video tool "customization" control desired by a user when applying the video tools. Tool construction methods using multiple mouse clicks are provided as an alternative to using drag-and-draw and one-click tools. Multi-click-plus tools give more specific information and provide a precise way to rapidly create customized tools.

19 Claims, 13 Drawing Sheets

OTHER PUBLICATIONS

*QVPAK 3D CNC Vision Measuring Machine User's Guide*, Version 7.0, 1st ed., Manual No. 99MCB225A, Series No. 359, Mitutoyo Corporation & Micro Encoder Inc., Kanagawa, Japan, Jan. 2003.

*QVPAK 3D CNC Vision Measuring Machine User's Guide*, Version 7.1, 2nd ed., Manual No. 99MCB225A1, Series No. 359, Mitutoyo Corporation & Micro Encoder Inc., Kanagawa, Japan, Sep. 2003.

* cited by examiner

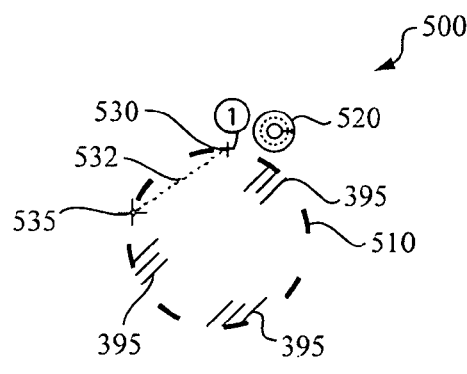
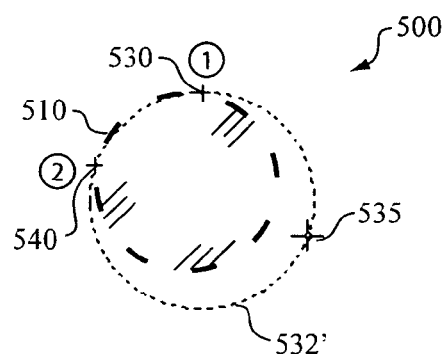
*Fig.5A.*  *Fig.5B.*
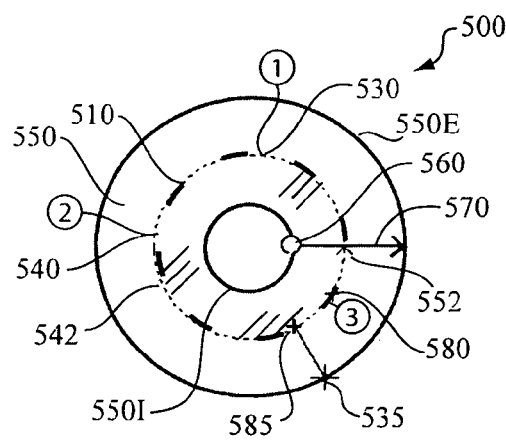
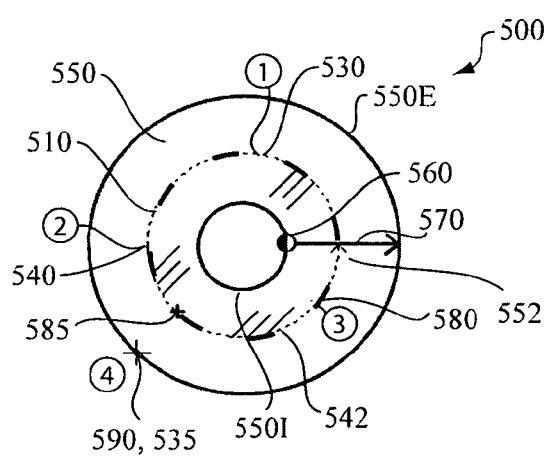
*Fig.5C.*  *Fig.5D.*

| | Tool Parameters | | | | | | |
|---|---|---|---|---|---|---|---|
| Tools, Operations | A | B | C | D | E | F | G |
| BOX tool & AUTO-TRACE tool MC+ | ROI Height end pt #1 (first click) | ROI Height end pt #2 (second click) | ROI Angular Orientation (second click) | ROI Width (symmetric about mid line) (third click) | Selector location (third click) | Scan direction (third click) | Sampling Direction (defaults from pt #1 to pt #2) (second click) |
| BOX tool & AUTO-TRACE tool MC | ROI Height end pt #1 (first click) | ROI Height end pt #2 (second click) | ROI Angular Orientation (second click) | ROI Width (symmetric about mid line) (default after last click) | Selector location (defaults near pt #1 after last click) | Scan direction (defaults based on scan at edge selector) | Sampling Direction (defaults from pt #1 to pt #2) (second click) |
| CIRCLE tool MC+ | Circle edge pt #1 (first click) | Circle edge pt #2 (second click) | Circle edge pt #3 (third click) | ROI Width (symmetric about mid line) (fourth click) | Selector location (fourth click) | Scan direction (fourth click) | Sampling Direction (defaults from pt #1 to pt #2) (third click) |
| CIRCLE tool MC | Circle edge pt #1 (first click) | Circle edge pt #2 (second click) | Circle edge pt #3 (third click) | ROI Width (symmetric about mid line) (default after last click) | Selector location (defaults near pt #1 after last click) | Scan direction (defaults based on scan at edge selector) | Sampling Direction (defaults from pt #1 to pt #2) (third click) |
| ARC tool MC+ | Arc edge & end pt #1 (first click) | Arc edge pt #2 (second click) | Arc edge & end pt #3 (third click) | ROI Width (symmetric about mid line) (fourth click) | Selector location (fourth click) | Scan direction (fourth click) | Sampling Direction (defaults from pt #1 to pt #2) (third click) |
| ARC tool MC | Arc edge & end pt #1 (first click) | Arc edge pt #2 (second click) | Arc edge & end pt #3 (third click) | ROI Width (symmetric about mid line) (default after last click) | Selector location (defaults near pt #1 after last click) | Scan direction (defaults based on scan at edge selector) | Sampling Direction (defaults from pt #1 to pt #2) (third click) |

*Fig.12A.*

| Tools, Operations | A | B | C | D | E | F | G |
|---|---|---|---|---|---|---|---|
| EDGE AUTOFOCUS tool MC+ | ROI Height end pt #1 (first click) | ROI Height end pt #2 (second click) | ROI Angular Orientation (horiz., vert., etc.) (second click) | ROI Width (symmetric about mid line) (third click) | | Scan direction (third click) | |
| EDGE AUTOFOCUS tool MC | ROI Height end pt #1 (first click) | ROI Height end pt #2 (second click) | ROI Angular Orientation (horiz., vert., etc.) (second click) | ROI Width Default (symmetric about mid line) (default after last click) | | Scan direction (default after last click) | |
| DUAL AREA CONTRAST tool MC+ | ROI Height end pt #1 (first click) | ROI Height end pt #2 (second click) | ROI Angular Orientation (second click) | ROI Width (symmetric about mid line) (third click) | | | |
| DUAL AREA CONTRAST tool MC | ROI Height end pt #1 (first click) | ROI Height end pt #2 (second click) | ROI Angular Orientation (second click) | ROI Width Default (symmetric about mid line) (default after last click) | | | |

*Fig.12B.*

ENHANCED VIDEO METROLOGY TOOL

CROSS-REFERENCE TO RELATED APPLICATION

This application claims the benefit of U.S. Provisional Application No. 60/648,956, filed Jan. 31, 2005, under the provisions of 35 U.S.C. § 119.

FIELD OF THE INVENTION

The invention relates generally to machine vision inspection systems, and more particularly to video metrology tools usable to define inspection operations for such systems.

BACKGROUND OF THE INVENTION

Precision machine vision inspection systems (or "vision systems" for short) can be utilized to obtain precise dimensional measurements of inspected objects and to inspect various other object characteristics. Such systems may include a computer, a camera and optical system, and a precision stage that is movable in multiple directions so as to allow the camera to scan the features of a workpiece that is being inspected. One exemplary prior art system that is commercially available is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the *QVPAK 3D CNC Vision Measuring Machine User's Guide*, published January 2003, and the *QVPAK 3D CNC Vision Measuring Machine Operation Guide*, published September 1996, each of which is hereby incorporated by reference in their entirety. This product, as exemplified by the QV-302 Pro model, for example, is able to use a microscope-type optical system to provide images of a workpiece at various magnifications, and move the stage as necessary to traverse the workpiece surface beyond the limits of any single video image. A single video image typically encompasses only a portion of the workpiece being observed or inspected, given the desired magnification, measurement resolution, and physical size limitations of such systems.

Machine vision inspection systems generally utilize automated video inspection. U.S. Pat. No. 6,542,180 teaches various aspects of such automated video inspection and is incorporated herein by reference in its entirety. As taught in the '180 patent, automated video inspection metrology instruments generally have a programming capability that allows an automatic inspection event sequence to be defined by the user for each particular workpiece configuration. This can be implemented by text-based programming, for example, or through a recording mode which progressively "learns" the inspection event sequence by storing a sequence of machine control instructions corresponding to a sequence of inspection operations performed by a user, or through a combination of both methods. Such a recording mode is often referred to as "learn mode" or "training mode." Once the inspection event sequence is defined in "learn mode," such a sequence can then be used to automatically acquire (and additionally analyze or inspect) images of a workpiece during "run mode."

The machine control instructions including the specific inspection event sequence (i.e., how to acquire each image and how to analyze/inspect each acquired image) are generally stored as a "part program" or "workpiece program" that is specific to the particular workpiece configuration. For example, a part program defines how to acquire each image, such as how to position the camera relative to the workpiece, at what lighting level, at what magnification level, etc. Further, the part program defines how to analyze/inspect an acquired image, for example, by using one or more video tools such as edge/boundary detection video tools.

Video tools may be used manually to accomplish manual inspection and/or machine control operations. Also, their setup parameters and operation can also be recorded during learn mode, in order to create automatic inspection programs, or "part programs". Such tools may include, for example, edge/boundary detection tools, shape or pattern matching tools, dimension measuring tools, coordinate establishing tools, and the like. For example, such tools are routinely used in a variety of commercially available machine vision inspection systems, such as the QUICK VISION® series of vision systems and the associated QVPAK® software, discussed above.

Video edge/boundary detection tools available in QVPAK® software include, for example, Point tool, Box tool, Circle tool, and Arc tool (see QVPAK 3D CNC Vision Measuring Machine User's Guide, incorporated by reference above). Briefly, a Point tool generates (locates) a data point at the intersection of a single scan line on an image. A Box tool generates a series of parallel scan lines, each of which returns a data point where an edge feature is found. A Circle tool generates a series of radial scan lines, over 360 centered about an origin, each of which returns a point where an edge feature is found. An Arc tool generates a series of radial scan lines centered about an origin, each of which returns a point where an edge feature is found (useful for returning data points from a rounded corner, for example). Each of these tools may be used to automatically detect a particular edge/boundary feature in an image.

Proper operation of a video tool depends on correct settings of various machine, image acquisition, and video tool parameters that affect the image quality and the operation of the video tool. For example, for an edge/boundary detection video tool to locate a target edge/boundary in an image, the machine and image acquisition parameters must set a correct level of lighting/brightness, proper focusing, proper magnification, etc. Video tool parameters, for example for an edge-detection video tool, may include a region of interest of (i.e., the region within a video image that the video tool searches), an edge selector, a scan direction, and other parameters are that set to properly control the operations of the video tool to locate the edge/boundary feature that is desired be detected.

The currently available features and graphical user interface (GUI) controls for video tools, and particularly dimensional metrology video tools, are limited. Some existing video tools require relatively few "setup" actions by the user, but have the disadvantage that many of the resulting video tool parameters are set to default values that may be inappropriate in many situations. Other existing video tools allow the video tool parameters to be extensively adjusted or customized by the user, but have the disadvantage that they require several independent setup actions by the user. Video tools that overcome these and other disadvantages would be desirable.

SUMMARY OF THE INVENTION

Currently, the users of precision machine vision inspection systems may spend a majority of their part-programming time setting up video tools and adjusting their parameters. Thus, even small improvements in their ease-of-use in comparison to their parameter customization capability, their GUI features, and other ergonomic factors, may be highly valued. The present invention is directed to novel and efficient instances of the video tools outlined above, as well as other video tools. A system and method for tool enhancements are provided which allow users to utilize video tools in a controlled manner. The video tools balance a minimal amount of cursor positioning and "mouse clicks" against a level of video tool "customization" control desired by a user when applying the video tools. Tool construction methods using multiple mouse clicks are provided as an alternative to using known drag-and-draw and one-click tool methods. The multi-click-plus and/or multi-click tools disclosed herein may convey more specific tool parameter information than known similar tools and provide a precise way to create tools. The multi-click-plus and/or multi-click tools disclosed herein may allow a user to determine a plurality of tool parameters with a single user action. These new video tool methods give users a high level of control over tool parameter creation with a simple and/or minimum set of user actions.

BRIEF DESCRIPTION OF THE DRAWINGS

The foregoing aspects and many of the attendant advantages of this invention will become more readily appreciated as the same become better understood by reference to the following detailed description when taken in conjunction with the accompanying drawings, wherein:

FIGS. 5A-5D are diagrams illustrating the operation of an exemplary circle tool on a circular feature;

FIGS. 12A and 12B are diagrams of a chart that illustrates operations for setting the parameters of various multi-click-plus and multi-click video tools.

DETAILED DESCRIPTION OF THE PREFERRED EMBODIMENT

Figure 1:
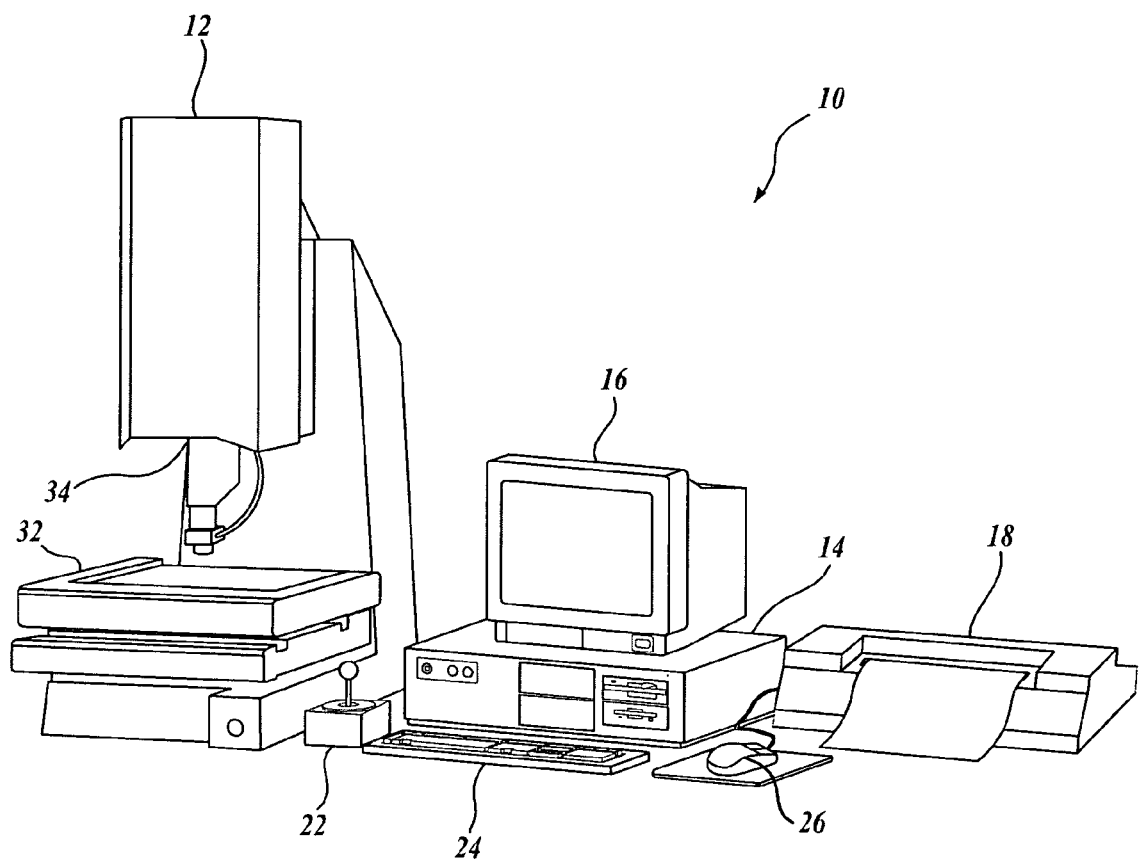
FIG. 1 is a diagram showing various typical components of a general purpose machine vision inspection system.

FIG. 1 is a block diagram of one exemplary machine vision inspection system 10 usable in accordance with the present invention. The machine vision inspection system 10 includes a vision measuring machine 12 that is operably connected to exchange data and control signals with a controlling computer system 14. The controlling computer system 14 is further operably connected to exchange data and control signals with a monitor or display 16, a printer 18, a joystick 22, a keyboard 24, and a mouse 26. The monitor or display 16 may display a user interface suitable for controlling and/or programming the operations of the machine vision inspection system 10.

The vision measuring machine 12 includes a moveable workpiece stage 32 and an optical imaging system 34 which may include a zoom lens or interchangeable lenses. The zoom lens or interchangeable lenses generally provide various magnifications for the images provided by the optical imaging system 34. The machine vision inspection system 10 is generally comparable to the QUICK VISION® series of vision systems and the QVPAK® software discussed above, and similar state-of-the-art commercially available precision machine vision inspection systems. The machine vision inspection system 10 is also described in copending and commonly assigned U.S. patent application Ser. No. 10/978,227, which is hereby incorporated by reference in its entirety. Various aspects of vision measuring machines and control systems are also described in more detail in copending and commonly assigned U.S. patent application Ser. Nos. 10/808,948, filed Mar. 25, 2004, and 10/632,823, filed Aug. 4, 2003, which are also hereby incorporated by reference in their entirety.

Figure 2:
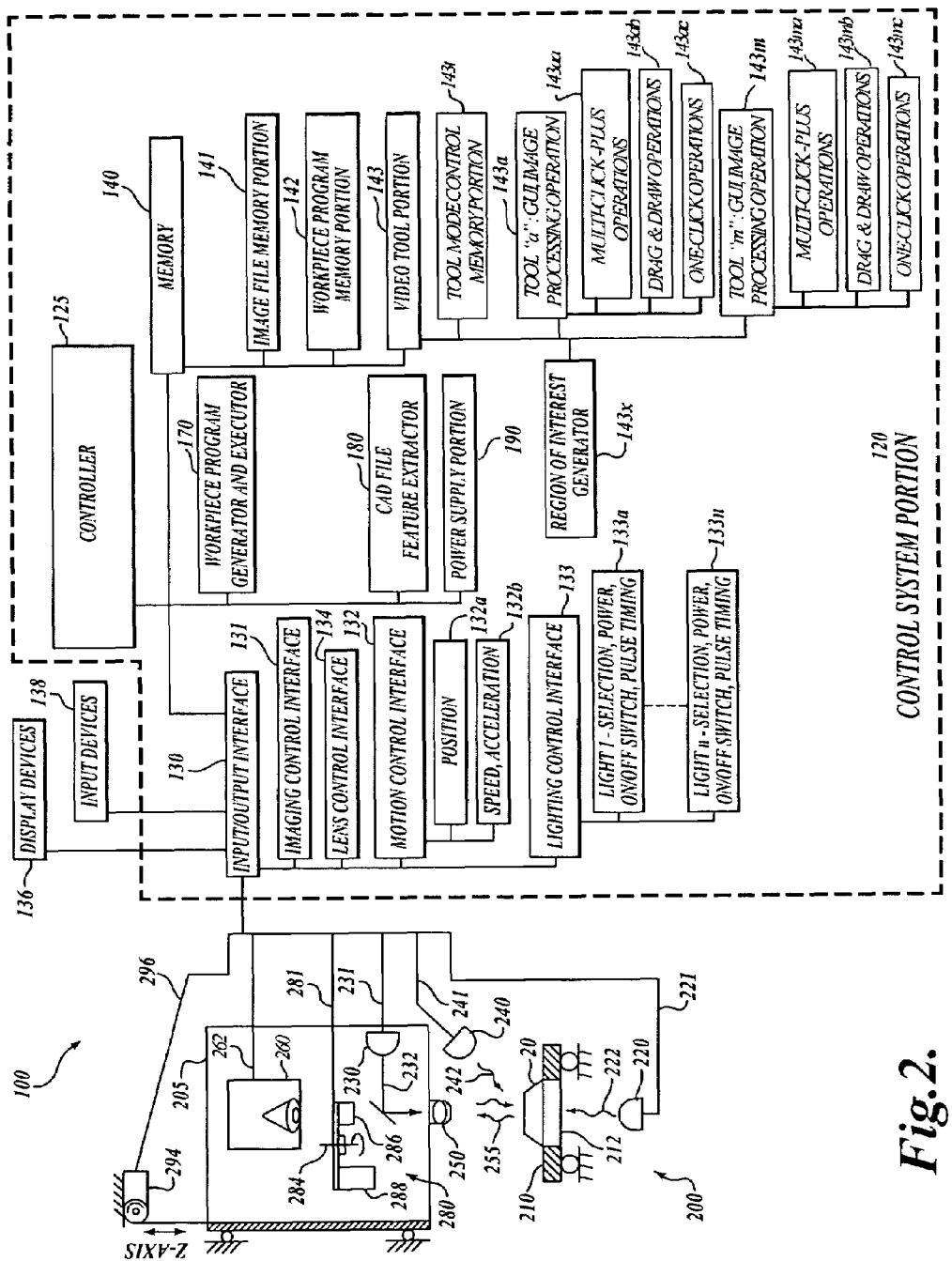
FIG. 2 is a diagram of a control system portion and a vision components portion of a machine vision inspection system.

FIG. 2 is a diagram of a control system portion 120 and a vision components portion 200 of a machine vision inspection system 100 in accordance with the present invention. As will be described in more detail below, the control system portion 120 is utilized to control the vision components portion 200. The vision components portion 200 includes an optical assembly portion 205, light sources 220, 230 and 240, and a workpiece stage 210 having a central transparent portion 212. The workpiece stage 210 is controllably movable along X and Y axes that lie in a plane that is generally parallel to the surface of the stage where a workpiece 20 may be positioned. The optical assembly portion 205 includes a camera system 260, an interchangeable objective lens 250, and may include a turret lens assembly 280, and the coaxial light source 230. Alternatively to the turret lens assembly, a fixed or manually interchangeable magnification-altering lens, or a zoom lens configuration, or the like, may be included. The optical assembly portion 205 is controllably movable along a Z axis that is generally orthogonal to the X and Y axes, by using a controllable motor 294, as described further below.

A workpiece 20 that is to be imaged using the machine vision inspection system 100 is placed on the workpiece stage 210. One or more of the light sources 220, 230, and 240 emits source light 222, 232, or 242, respectively, that is usable to illuminate the workpiece 20. Light emitted by the light sources 220, 230, and/or 240 illuminates the workpiece 20 and is reflected or transmitted as workpiece light 255, which passes through the interchangeable objective lens 250 and the turret lens assembly 280 and is gathered by the camera system 260. The image of the workpiece 20, captured by the camera system 260, is output on a signal line 262 to the control system portion 120.

The light sources 220, 230, and 240 that are used to illuminate the workpiece 20 can include a stage light 220, a coaxial light 230, and a surface light 240, such as a ring light or a programmable ring light, all connected to the control system portion 120 through signal lines or busses 221, 231, and 241, respectively. As a primary optical assembly of the machine vision inspection system 100, the optical assembly portion 205 may include, in addition to the previously discussed components, other lenses, and other optical elements such as apertures, beam-splitters and the like, such as may be needed for providing coaxial illumination, or other desirable machine vision inspection system features. When it is included as a secondary optical assembly of the machine vision inspection system 100, the turret lens assembly 280 includes at least a first turret lens position and lens 286 and a second turret lens position and lens 288. The control system portion 120 rotates the turret lens assembly 280 along axis 284, between at least the first and second turret lens positions, through a signal line or bus 281.

The distance between the workpiece stage 210 and the optical assembly portion 205 can be adjusted to change the focus of the image of the workpiece 20 captured by the camera system 260. In particular, in various exemplary embodiments, the optical assembly portion 205 is movable in the vertical Z axis direction relative to the workpiece stage 210 using a controllable motor 294 that drives an actuator, a connecting cable, or the like, to move the optical assembly portion 205 along the Z axis. The term Z axis, as used herein, refers to the axis that is intended to be used for focusing the image obtained by the optical assembly portion 205. The controllable motor 294, when used, is connected to the input/output interface 130 via a signal line 296.

As shown in FIG. 2, in various exemplary embodiments, the control system portion 120 includes a controller 125, an input/output interface 130, a memory 140, a workpiece program generator and executor 170, a CAD file feature extractor 180, and a power supply portion 190. It will be appreciated that each of these components, as well as the additional components described below, may be interconnected by one or more data/control buses and/or application programming interfaces, or by direct connections between the various elements.

The input/output interface 130 includes an imaging control interface 131, a motion control interface 132, a lighting control interface 133, and a lens control interface 134. The motion control interface 132 includes a position control element 132a, and a speed/acceleration control element 132b. However, it should be appreciated that in various exemplary embodiments, such elements may be merged and/or indistinguishable. The lighting control interface 133 includes lighting control elements 133a-133n, which control, for example, the selection, power, on/off switch, and strobe pulse timing if applicable, for the various corresponding light sources of the machine vision inspection system 100, such as the light sources 220, 230, and 240.

The memory 140 includes an image file memory portion 141, a workpiece program memory portion 142 that may include one or more part programs, or the like, and a video tool portion 143. The video tool portion 143 includes tool portions 143a-143m, which determine the GUI, image processing operation, etc., for each of the corresponding tools. Each of the tool portions 143a-143m includes respective mode portions that determine its behavior depending on whether or not that tool is activated in that particular mode. For example, the tool portion 143a includes a multi-click-plus operations portion 143aa that determines the behavior of the tool when it is activated in a multi-click-plus mode, described in greater detail below, a drag-and-draw operations portion 143ab that determines the behavior of the tool when it is activated in a known drag-and-draw mode, and a one-click operations portion 143ac that determines the behavior of the tool when it is activated in a known one-click mode. Any or all of the other tools of the video tool portion 143 may include similar mode portions, for example the final tool portion 143m similarly includes a multi-click-plus operations portion 143ma, a drag-and-draw operations portion 143mb, and a one-click operations portion 143mc. The video tool portion 143 also includes a tool mode control memory portion 143t that governs the overall selection and operation of the respective tools modes referred to above. The video tool portion 143 also includes a region of interest generator 143x that supports automatic, semi-automatic and/or manual operations that define various regions of interest that are operable in various video tools included in the video tool portion 143.

In general, the memory portion 140 stores data usable to operate the vision system components portion 200 to capture or acquire an image of the workpiece 20 such that the acquired image of the workpiece 20 has desired image characteristics. The memory portion 140 further stores data usable to operate the machine vision inspection system 100 to perform various inspection and measurement operations on the acquired images, either manually or automatically, and to output the results through the input/output interface 130. The memory portion 140 also contains data defining a graphical user interface operable through the input/output interface 130.

The signal lines or busses 221, 231 and 241 of the stage light 220, the coaxial light 230, and the surface light 240, respectively, are all connected to the input/output interface 130. The signal line 262 from the camera system 260 and the signal line 296 from the controllable motor 294 are connected to the input/output interface 130. In addition to carrying image data, the signal line 262 may carry a signal from the controller 125 that initiates image acquisition.

One or more display devices 136 and one or more input devices 138 can also be connected to the input/output interface 130. The display devices 136 and input devices 138 can be used to display a user interface, which may include various graphical user interface (GUI) features that are usable to perform inspection operations, and/or to create and/or modify part programs, to view the images captured by the camera system 260, and/or to directly control the vision system components portion 200. In a fully automated system having a predefined part program (or workpiece program), the display devices 136 and/or the input devices 138 may be omitted.

With regard to the CAD file feature extractor 180, information, such as a CAD file representing a workpiece is frequently available in industrial applications of machine vision inspection systems. The locations of edges and boundaries in the CAD file representation may be determined manually, in a semi-automated fashion, or fully automatically, in such information may be useful for workpiece programming or navigating to a desired workpiece feature.

In various exemplary embodiments, when a user utilizes the machine vision inspection system 100 to create a workpiece image acquisition program for the workpiece 20, the user generates workpiece program instructions either by explicitly coding the instructions automatically, semi-automatically, or manually, using a workpiece programming language, or by generating the instructions by moving the machine vision inspection system 100 through an image acquisition training sequence such that the workpiece program instructions capture the training sequence. This process is repeated for multiple images in a set of images that are to be captured. These instructions, when executed, will cause the machine vision inspection system to manipulate the workpiece stage 210 and/or the camera system 260 at certain speed(s) such that a particular portion of the workpiece 20 is within the field of view of the camera system 260 and at a desired focus state for each of a set of images to be acquired. In addition to the program instructions that control the relative movement of the camera and the workpiece, the workpiece image acquisition program also needs to include program instructions that activate one or more of the light sources 220-240 to provide a desired illumination of the workpiece 20 during each image acquisition.

Once a set of workpiece image acquisition instructions are defined, the control system 120 executes the instructions and commands the camera system 260 to capture one or more images of the workpiece 20 according to the instructions. The control system 120 will then, under control of the controller 125, input the captured image(s) through the input/output interface 130 and store the captured image(s) in the memory 140. The controller 125 may also display the captured images on the display device 136.

The control system portion 120 is further usable to recall captured and stored workpiece inspection images, to inspect and analyze workpiece features in such workpiece inspection images, and to store and/or output the inspection results. These analysis and inspection methods are typically embodied in various video tools included in the video tool portion 143 of the memory 140. Some of these tools, including edge detection tools, shape or pattern matching tools, dimension measuring tools, coordinate matching tools, auto focus tools, and the like, for example, are routinely available in a variety of commercially available machine vision inspection systems, such as the QUICK VISION® series of vision systems and the associated QVPAK® software, discussed above. The various methods disclosed herein may be applied to define the video tool parameters used these and other video tools in a novel and more convenient manner. For example, parameters associated with the edge/boundary detection tools disclosed in co-pending and commonly assigned U.S. patent application Ser. No. 09/987,986, filed Nov. 16, 2001, and the improved autofocus tools and methods described in co-pending U.S. patent application Ser. No. 10/719,210, filed Nov. 24, 2003, each of which is hereby incorporated by reference in its entirety, may also be defined according to the methods and user interface features disclosed herein.

After the image inspection/analysis operation using one or more of these video tools is completed, the control system 120 outputs the results of each analysis/inspection operation to the input/output interface for outputting to various display devices 136, such as a video display, printer, and the like. The control system 120 may also store the results of each inspection operation in the memory 140.

Figures 3A, 3B, 3C:
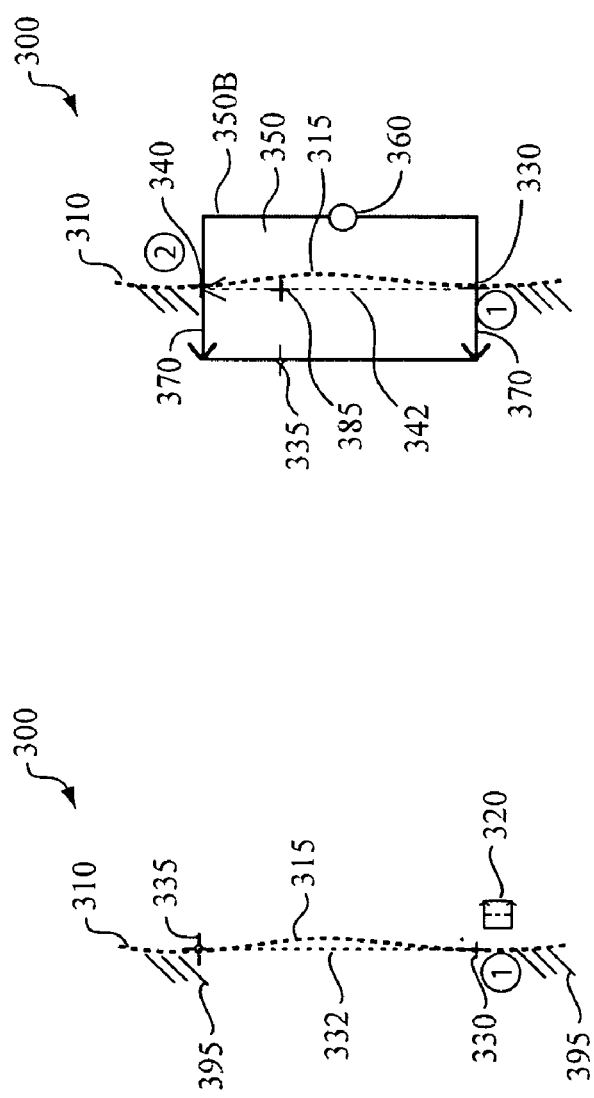
FIGS. 3A-3C are diagrams illustrating the operation of an exemplary box tool on an imperfect edge feature.

FIGS. 3A-3C are diagrams illustrating the operation of an exemplary box tool 300 according to this invention, on an imperfect edge feature 310. In FIGS. 3A-3C, as well as figures described below, shading lines typified by the shading lines 395 are provided for purposes of illustration, to indicate which side of the edge feature 310, or another edge feature illustrated herein, is darker in an image. This edge characteristic is significant for many edge finding video tools that include a parameter that indicates whether the tool operations should search for an edge feature that transitions from a dark-to-light region, or light-to-dark region, along a particular scan direction, as will be described in more detail below.

In operation, in an exemplary tool mode referred to as "multi-click-plus" herein, when the box tool icon on a video tool bar is selected, as described below with reference to FIG. 11, a box tool indicator 320, as shown in FIG. 3A, may appear on the display. The box tool indicator 320 may be associated with a cursor, which may appear as a cross-hair, or the like at a "cursor point". The cursor point may provide coordinates that are used by the box tool to determine various parameters of the box tool and/or to adjust various features or parameter indicators of the box tool GUI, as described in greater detail below. In general, for the various tools shown and described herein, a tool indicator may continue to appear adjacent to the cursor throughout various operations described herein, even if it is omitted from a figure in order to more clearly illustrate other features of the figure.

In the example shown in FIG. 3A, the user initially places a point 1 along the edge feature 310 at a desired position 330, which bounds one end of the box tool height, that is, the height of the box tool region of interest 350 (box tool ROI 350), shown in FIGS. 3B and 3C. Unless otherwise indicated by description or context, throughout this disclosure, "placing a point" may generally comprise the user entering the coordinates of a desired point, to be used by a video tool for determining one or more video tool parameters. In this way the user may control the determination or definition of various video tool parameters. For example, in exemplary embodiments, the user may generally move an input device, such as a mouse, joystick, trackball, or the like, to move the cursor around on a display of a feature such as the edge feature 310. When the user has positioned the cursor at a desired position, the user may then click an input device button, or press "enter" on a keyboard, or the like, in order to "place a point" at the desired position. Placing a point may anchor a tool parameter indicator at the position of the placed point, as described below.

After placing the point 1, a parameter indicator, such as a crosshair, may be anchored at the point 1, and the user may then continue to move the cursor 335, which, in some embodiments, may be connected to the parameter indicator anchored at point 1 (at position 330) by a dotted construction line 332, that may follow the cursor 335 like a taut elastic band. In other embodiments, the construction line is not included, and the cursor may act as a parameter indicator. As shown in FIG. 3A, the user has moved the cursor 335 to a second point along the edge feature 310, which tentatively bounds the other end of the box tool ROI height. The cursor, or the moving end of the construction line 332, may be regarded as a parameter indicator, since it is reflecting a potential dimension of a region of interest of the box tool 300, which will be fixed when the user places a second point, as described below. In exemplary embodiments, a parameter indicator (e.g. the end of the construction line, or a cross-hair associated with the cursor position, or the like) may be automatically linked to be dynamically adjusted based on the cursor position (which is controlled by the user's input device movement), without requiring the user to take, or maintain, any special action. That is, "automatic linking", as the term is used herein, means that the user need not "select" the dynamically adjusted parameter indicator with an additional mouse click after placing the preceding point, and/or the user need not continue to depress and/or hold down a mouse button, or other input device button, or the like, to "drag" the dynamically adjusted parameter indicator, or the like.

Regarding "automatic linking", automatic linking is one feature that makes the box tool 300, and various other tools described herein, particularly convenient to use, and in conjunction with the appearance and operation of the parameter indicators shown and described herein, particularly intuitive to learn and use. In embodiments where automatic linking is used, the need for the user to "select" a dynamically adjusted parameter indicator, is eliminated, which provides that an operation such as a "button click" may be reserved to operate exclusively as an operation that places a point while the video tool parameters are being established by the user. Otherwise, a "click" might be required to select a parameter indicator that is to dynamically follow the cursor, or the like. Thus, the user may learn more quickly by associating one operation (e.g., a "click") with one function (placing a point) while operating the video tool GUI. Furthermore, in other conventional "drag and draw" operations, a first point (e.g., a box corner) is "placed" by depressing a mouse button, or the like, then the button must be held in an unstable depressed state while moving to a next desired location (e.g., the other corner of the box), and then the next desired location is placed by releasing the button. Thus, two sequential placed points are placed by two different actions. In contrast, automatic linking provides that all sequentially placed points may be placed by the same type of operation, and that a button need not be held in an unstable state. Thus, in embodiments that use automatic linking, the user may avoid an unstable ergonomic state, and may also learn more quickly by associating one type of operation (e.g., a "click") with one function (e.g., placing a point) while operating the video tool GUI.

Continuing, as shown in FIG. 3B, the user places a point 2 at a position 340, which anchors the other end of the box tool ROI height (or longitudinal dimension) and may cause other parameter indicators of the box tool 300 to appear and be automatically linked to be dynamically adjusted based on the cursor position. The term "parameter indicators" is used herein to refer to the graphical features of the user interface of a video tool, or a video tool GUI, that correspond to the current user-determined, or machine determined or derived, or default tool parameters. For example, the parameter indicators shown in FIGS. 3B and 3C may include the upper end, lower end, and sides of the ROI box 350B, the scan direction arrows 370, the midline indicator 342, the sampling direction indicator (which is the upward pointing arrowhead located along the midline 342 at the position 340), the edge selector location indicator 385 (also called the selector location indicator 385), and the rising/falling indicator 360. The rising/falling indicator 360 is empty, indicating that the rising/falling direction has not yet been determined in FIG. 3B. At various times, the cursor display may be merged with, or indistinguishable from, various parameter indicators of the video tool GUI. This might alternatively be described, or implemented, as using the cursor as a parameter indicator in the GUI at various times, or as the cursor representation changing to indicate various parameters, or as the various parameter indicators "following" the cursor. All of these descriptions may fall within the scope of this invention, if they serve to implement the various features and operations of the invention outlined herein.

Regarding "linking" in general, as the term is used herein, for some "linked" parameter indicators, they may be dynamically adjusted to follow the cursor position. For some linked parameter indicators, they may be dynamically adjusted in a manner depending on the cursor position, without following the cursor. As one example, a first side of the ROI box 350B may be dynamically adjusted to follow the cursor position, while the other side of the ROI box 350B may dynamically adjusted to a location symmetric to first side, about the centerline 342 of the box tool 300. As another example, the direction of the scan direction arrows 370 may dynamically adjusted based on the cursor position (e.g., to point along a direction that is from the centerline toward the cursor position), regardless of their location, which may be an anchored location. As another example, the location of the edge selector location indicator 385 may be dynamically adjusted to parallel the cursor position, while being restricted to travel along the centerline 342.

For the example shown in FIG. 3B, when point 2 is placed, thereafter the video tool 300 determines the width (or lateral dimension) of the ROI box 350B as being located symmetrically about the centerline 342 joining point 1 and point 2. Also, the point placement sequence determines a sampling direction proceeding from point 1 to point 2, as indicated by the upward-pointing sampling direction arrow at the position 340. The sampling direction is the direction that data sampling and/or analysis follows when determining a series of edge points along the edge feature 310.

After placing point 2, the user may continue to move the cursor 335. In exemplary embodiments, the automatically linked parameter indicators may be dynamically adjusted based on the cursor position without requiring the user to depress and/or hold down a mouse button. As shown in FIG. 3B, after placing point 2, and the appearance of the various parameter indicators discussed above, the user has moved the cursor 335 to a point down and to the left from point 2, and the automatically linked width of the ROI box 350B, selector location indicator 385, and scan direction arrows 370, have been dynamically adjusted accordingly.

It should be appreciated that the linked width of the ROI box 350B, the linked selector location indicator 385, and the linked scan direction arrows 370, may all be linked and dynamically adjusted at the same time. Linking a plurality of different types of parameter indicators to be dynamically adjusted at the same time is another feature that makes the box tool 300, and various other tools described herein, particularly convenient to use, and, in conjunction with the appearance and operation of the parameter indicators shown and described herein, particularly intuitive to learn and use. This may be the case, even if the plurality of different types of parameter indicators are linked by operations that are not automatic. However, the combination of automatically linking a plurality of different parameter indicators to be dynamically adjusted at the same time is particularly convenient and intuitive, and may be preferred in many embodiments.

Regarding the positioning of the edge selector location indicator 385, the edge feature 310 is shown to include a deviating portion 315. Edge deviations, such as the deviating portion 315, may generally create potential problems for properly training an edge-finding tool. It will be appreciated that workpiece edges in actual workpiece images may exhibit significant variations along the edge, due to lighting or shadow variations, contamination effects, diffraction effects, and the like. For example, diffraction effects and/or shadows may frequently create a closely-spaced "family" of edge-like image features adjacent to the true workpiece edge location in the image. Properly "training" an edge tool during learn mode operations is critical to locating the proper edge among these potential erroneous edge-like features, during subsequent inspection operations. During training, an edge tool analyzes the pixel intensity variations along a scan line, and determines and records the particular intensity variation characteristics that correspond to the desired edge. For example, these characteristics may be based on the total intensity variation across the edge, the rate of change of the intensity variation across the edge, whether the intensity variation is rising or falling across the edge for a particular scan direction, whether the intensity variation is the first, second, third, etc. rising or falling variation along the scan line, etc. An edge tool may be "trained" by automatically determining and recording these characteristics by analyzing a desired "prototypical" edge scan. In various embodiments, a user may pick the desired location for the prototypical edge scan by locating the selector location indicator 385 on the desired edge, preferably at a location that is relatively free of contamination, optical aberrations, and the like. In FIG. 3B, for purposes of illustration, the cursor 335 has been temporarily located at a point such that the linked selector location indicator 385, which may traverse along the centerline 342 to parallel the location of the cursor 335, is located slightly away from the edge 310 due to the deviating portion 315. Such a selector location may lead to erroneous training.

As shown in FIG. 3C, the user has continued to move the cursor 335 and the automatically linked width of the ROI box 350B, selector location indicator 385, and scan direction arrows 370, have been dynamically adjusted accordingly. The selector location now coincides with a desired prototypical scan location on the edge 310, and the scan direction arrows 370 point along a desired direction. Since the cursor 335 is on the right side of the centerline 342, the arrows 370 are shown to be pointing from left to right. Regarding the scan direction, for increased reliability it is generally advantageous to determine the scan direction to proceed from a region where the intensity is more uniform to a region that may have more intensity variation (due to texture or image noise, for example), such that a desired edge transition characteristic is determined along a scan line before unpredictable "noise" characteristics are encountered.

When the user places point 3, various parameter indicators are anchored and/or fixed based on the position of the placed point 3, and any previously undetermined tool parameters associated with the final set of parameter indicators are determined and used such that the tool may be run to automatically teach or train the tool. After the tool is trained, the rising/falling indicator 360 may be automatically filled with dark and light regions as shown in FIG. 3C, reflecting the direction of the dark-to-light transition that was determined by the tool operations during training. Subsequently, a series of edge points that are detected along the edge 310 based on the trained parameters may be marked on the display, for example using the known methods employed in commercially available machine vision systems. The user may then accept the training results and continue to other operations, or reject the training results, further modify the tool parameters, and retrain the tool until satisfactory results are achieved.

It should be appreciated that in various embodiments, an auto-trace tool, such as that indicated in FIG. 12A, and included in various commercial machine vision inspection systems, may include tool parameters that may be defined by operations substantially similar to those previously described with reference to the box tool 300. Thus, it should be appreciated that one skilled in the art may design and operate an auto-trace tool based on this disclosure in conjunction with known auto-trace tool techniques found in commercially available machine vision inspection systems.

Figure 4:
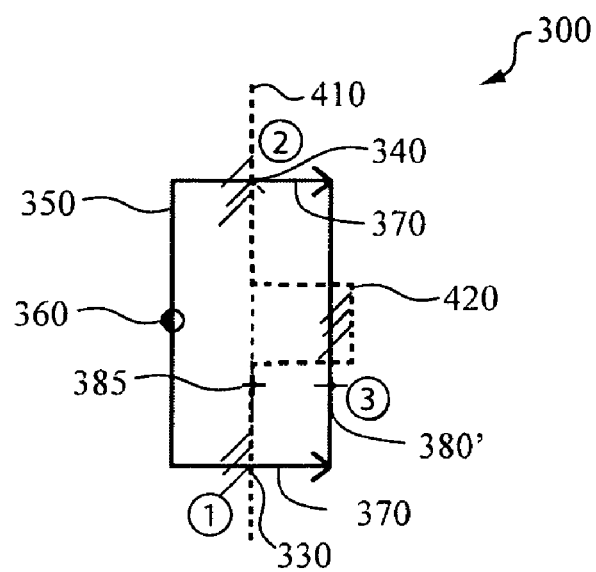
FIG. 4 is a diagram illustrating the operation of the exemplary box tool of FIG. 3, on a notched edge feature.

FIG. 4 is a diagram illustrating an advantage of the operation of the box tool 300 on an edge feature 410 with an interruption 420. As will be described in more detail below, the operation of the box tool 300 in accordance with the present invention is advantageous in that edge features with unusual characteristics (e.g., a notch or protrusion) can be readily accommodated with a small or minimum number of user actions. The operation of the box tool 300 of FIG. 4 is similar to the operation of the box tool 300 as described above with respect to FIGS. 3A-3C. The three points 1, 2, and 3, are placed at the locations 330, 340, and 380', in a manner similar to that described above. However, in the example shown in FIG. 4, it is desired to find the location of the straight portion of the edge 410 that does not include the interruption 420. Thus, the point 3 is placed at a location 380' that insures that the interruption 420 will not disturb the training of the box tool 300 or subsequent edge finding operations. In particular, the point 3 is placed such that the linked width dimension of the box tool ROI 350 is adjusted so as to exclude the interruption 420 and such that the linked selector location indicator 385 is located at a desired location away from the interruption 420 on the straight portion of the edge 410, so that the trained box tool 300 will operate as desired. It should be appreciated that the width of the box tool ROI 350 and the selector location indicator 385 are both automatically linked to be dynamically adjusted based on the cursor location as described with reference to FIG. 3C, and finally to be anchored based on the placed point 3 as shown in FIG. 4, such that they both avoid the interruption 420 with a single user action that anchors point 3.

FIGS. 5A-5D are diagrams illustrating the operation of a circle tool 500 on a circular edge feature 510. The operation of the various features of the circle tool 500 are analogous to the similar features of the box tool 300 as described above with respect to FIGS. 3A-3C, unless otherwise indicated by description or context. In operation, in a tool mode referred to as "multi-click-plus" herein, when the circle tool icon on a video tool bar is selected, as described below with reference to FIG. 11, a circle tool indicator 520, as shown in FIG. 5A, may appear on the display. The circle tool indicator 520 may be associated with a cursor point, as previously described with reference to the box tool indicator 320. In the example shown in FIG. 5A, the user initially places a point 1 along the edge feature 510 at a desired position 530. After placing the point 1, a parameter indicator, such as a crosshair, may be anchored at the point 1, and the user may then continue to move the cursor 535, which, in some embodiments, may be connected to the parameter indicator anchored at point 1 (at position 530) by a dotted construction line 532, that may follow the cursor 535 like a taut elastic band. The moving end of the construction line 532, may be regarded as a parameter indicator that is automatically linked to be dynamically adjusted based on the cursor position. In exemplary embodiments, the construction line 532 may follow the cursor position without requiring the user to depress and/or hold down a mouse button. As shown in FIG. 5A, the user has moved the cursor 535 to a second point along the edge feature 510.

Continuing, as shown in FIG. 5B, the user places a point 2 at a position 540 on the edge feature 510, which may anchor another parameter indicator and may cause other parameter indicators of the circle tool 500, such as the provisional circle construction line 532', to appear. After placing point 2, the user may continue to move the cursor 535. In the example shown in FIG. 5B, after placing point 2, the provisional circle construction line 532', is automatically linked to be dynamically adjusted to be best fit to point 1, point 2, and the position of the cursor 535, without requiring the user to depress and/or hold down a mouse button after placing point 2.

Continuing, as shown in FIG. 5C, the user places a point 3 at a position 580 on the edge feature 510, which may anchor another parameter indicator and/or and may cause other parameter indicators of the circle tool 500 to appear. The provision circle construction line 532' may be replaced by, or dynamically adjusted to become, an anchored nominal circle indicator 542 which is also the circle tool ROI centerline indicator 542. The nominal circle indicator 542 may have a radius and center location that are best fit to point 1, point 2 and point 3, and that nominally approximates the edge feature 510. A sampling direction may proceed around the circle in the direction from point 1 to point 2, as indicated by an anchored sampling direction indicator, the arrowhead 552, pointing counterclockwise on the circle tool ROI centerline indicator 542. Other exemplary parameter indicators shown in FIG. 5C include the circle tool ROI interior radius or diameter 550I and exterior radius or diameter 550E, a scan direction arrow 570, a selector location indicator 585, and a rising/falling indicator 560. In exemplary embodiments, these other parameter indicators may be automatically linked to be dynamically adjusted based on the cursor position, without requiring the user to depress and/or hold down a mouse button.

For the example shown in FIG. 5C, when point 3 is placed, thereafter the automatically linked radial dimension of the circle tool ROI 550, the selector location indicator 585, and the radial edge scan orientation indicated by the scan direction indicator arrow 570 are dynamically adjusted based on the cursor position. The radial edge scan orientation may be a function of the location of the cursor 535 relative to the circle tool ROI centerline indicator 542. In the example shown in FIG. 5C, the user has moved the cursor 535 to a point down from the placed point 3, and the location of the ROI diameter 550E, the radial dimension of the circle tool ROI 550, selector location indicator 585, and scan direction arrows 570, have been dynamically adjusted accordingly. Since the location of the cursor 535 is outside of the circle tool ROI centerline indicator 542, the scan direction as indicated by the scan direction indicator arrow 570 is radially outward, whereas if the cursor 535 was moved inside the circle tool ROI centerline indicator 542, the scan direction would be reversed. In the embodiment shown in FIG. 5C, the exterior diameter 550E is dynamically adjusted to follow the cursor 535, and the radial dimension of the circle tool ROI 550 is dynamically adjusted symmetrically about the ROI centerline indicator 542. However, in other exemplary embodiments, the circle tool ROI interior diameter 550I and/or exterior diameter 550E may be subsequently or independently adjusted such that the radial dimension of the circle tool ROI 550 is not symmetrical about the ROI centerline indicator 542.

As shown in FIG. 5D, the user has continued to move the cursor 535 to the location 590, and the automatically linked radial dimension of the circle tool ROI 550, selector location indicator 585, and scan direction arrow 570, have been dynamically adjusted accordingly. The location of the selector location indicator 585 now coincides with a desired prototypical scan location on the edge feature 510, and the scan direction arrow 570 is oriented along the desired radial direction.

When the user places point 4 at the location 590, various parameter indicators are anchored and/or fixed based on the position of the placed point 4, and any previously undetermined tool parameters associated with the final set of parameter indicators are determined and used such that the tool may be run to automatically teach or train the tool. After the tool is trained, the rising/falling indicator 560 may be automatically filled with dark and light regions as shown in FIG. 5D, reflecting the direction of the dark-to-light transition that was determined by the tool operations during training. Subsequently, a series of edge points that are detected along the edge feature 510 based on the trained parameters may be marked on the display, for example using the known methods employed in commercially available machine vision systems. The user may then accept the training results and continue to other operations, or reject the training results, further modify the tool parameters, and retrain the tool until satisfactory results are achieved.

Figure 6:
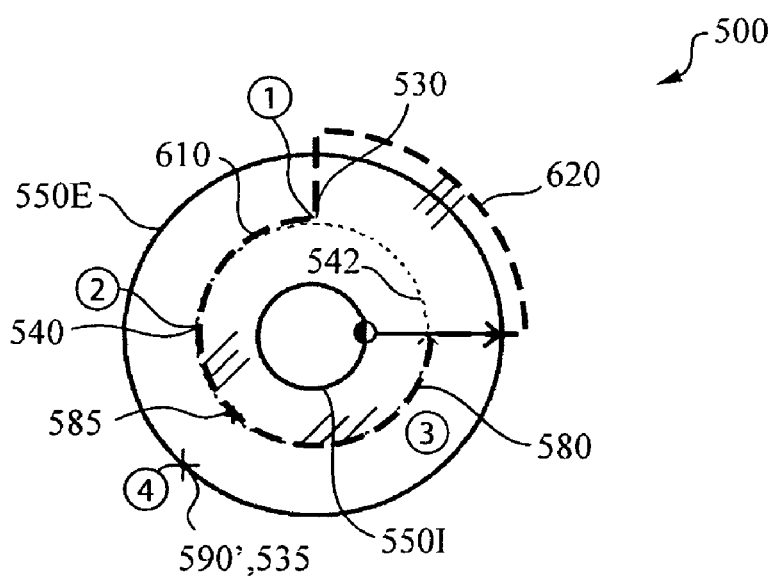
FIG. 6 is a diagram illustrating the operation of the exemplary circle tool of FIG. 5, on a notched circular feature.

FIG. 6 is a diagram illustrating an advantage of the operation of the circle tool 500 on a circular edge feature 610 with an interruption 620. As will be described in more detail below, the operation of the circle tool 500 in accordance with the present invention is advantageous in that circular edge features with unusual characteristics (e.g., a notch or protrusion) can be readily accommodated with a small or minimum number of user actions. The operation of the circle tool 500 of FIG. 6 is similar to the operation of the circle tool 500 as described above with respect to FIGS. 5A-5D. The three points 1, 2, and 3, are placed at the locations 530, 540, and 580, in a manner similar to that described above. However, in the example shown in FIG. 6, it is desired to find the location of the circular portion of the edge feature 610 that does not include the interruption 620. Thus, the point 4 is placed at a location 590' that insures that the interruption 620 will not disturb the training of the circle tool 500 or subsequent edge finding operations. In particular, the point 4 is placed such that the linked radial dimension of the circle tool ROI 550 is adjusted so as to exclude the interruption 620, and such that the linked selector location indicator 585 is located at a desired location away from the interruption 620 on a portion of the desired edge feature 610, so the trained circle tool 500 will operate as desired. It should be appreciated that the radial dimension of the circle tool ROI 550 and the selector location indicator 585 are both automatically linked to be dynamically adjusted based on the cursor location as described with reference to FIG. 5C, and finally to be anchored based on the placed point 4 as shown in FIG. 6, such that they both avoid the interruption 620 with a single user action that anchors point 4.

Figure 7A:
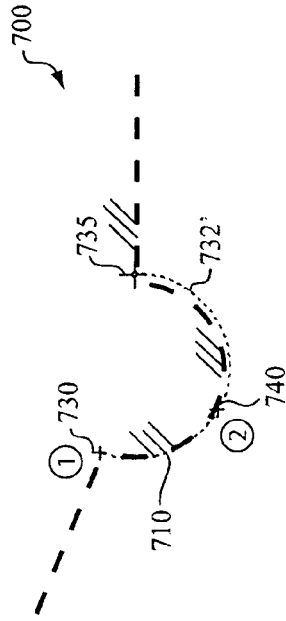
FIGS. 7A-7D are diagrams illustrating the operation of an exemplary arc tool on an arc feature.

FIGS. 7A-7D are diagrams illustrating the operation of an arc tool 700 on an arc-shaped edge feature 710. The operation of the various features of the arc tool 700 are analogous to the similar features of the circle tool 500 as described above with respect to FIGS. 5A-5D, unless otherwise indicated by description or context. In operation, in a tool mode referred to as "multi-click-plus" herein, when the arc tool icon on a video tool bar is selected, as described below with reference to FIG. 11, an arc tool indicator 720, as shown in FIG. 7A, may appear on the display. The arc tool indicator 720 may be associated with a cursor point, as previously described with reference to the box tool indicator 320. In the example shown in FIG. 7A, the user initially places a point 1 at a desired position 730 at one end of the arc on the edge feature 710. After placing the point 1, a parameter indicator, such as a crosshair, may be anchored at the point 1, and the user may then continue to move the cursor 735, which may be connected to the parameter indicator anchored at point 1 (at position 730) by a dotted construction line 732, that may follow the cursor 735 like a taut elastic band. The moving end of the construction line 732, may be regarded as a parameter indicator that is automatically linked to be dynamically adjusted based on the cursor position. In exemplary embodiments, the construction line 732 may follow the user's mouse movement without requiring the user to depress and/or hold down a mouse button. As shown in FIG. 7A, the user has moved the cursor 735 to a second point along the edge feature 710.

Figure 7B:
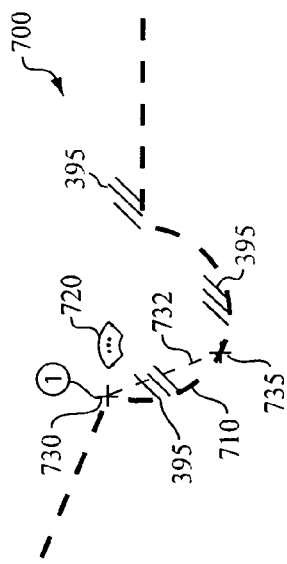

Continuing, as shown in FIG. 7B, the user places a point 2 at a position 740 on the edge feature 710, which may anchor another parameter indicator and may cause other parameter indicators of the arc tool 700, such as the provisional arc construction line 732', to appear. After placing point 2, the user may continue to move the cursor 735. In the example shown in FIG. 7B, after placing point 2, the provisional arc construction line 732' is automatically linked to be dynamically adjusted to be best fit to point 1, point 2, and the position of the cursor 735, without requiring the user to depress and/or hold down a mouse button after placing point 2. In other embodiments, the construction line is not included, and the cursor may act as a parameter indicator. The cursor, or the moving construction line 732', may be regarded as a parameter indicator, since it is reflecting a potential parameter of a region of interest of the arc tool 700, which will be fixed when the user places a third point, as described below.

Figure 7C:
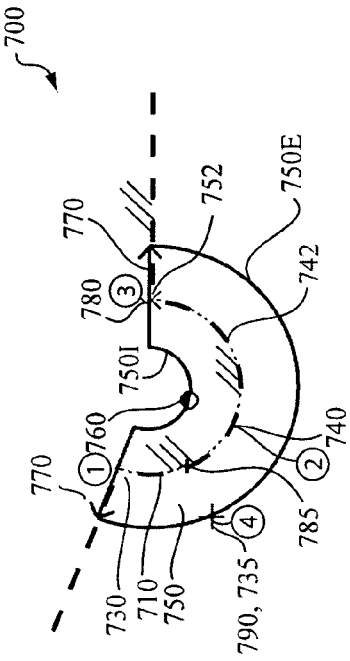

Continuing, as shown in FIG. 7C, the user places a point 3 at a desired position 780 at the other end of the arc on the edge feature 710, which may anchor another parameter indicator and/or and may cause other parameter indicators of the arc tool 700 to appear. The provisional arc construction line 732' may be replaced by, or dynamically adjusted to become, an anchored nominal arc indicator 742, which is also the arc tool ROI centerline indicator 742. The nominal arc indicator 742 may have a radius and center location that are best fit to point 1, point 2 and point 3, and that nominally approximates the edge feature 710. A sampling direction may proceed around the arc in the direction from point 1 to point 2, as indicated by an anchored sampling direction indicator, the arrowhead 752, pointing counterclockwise on the arc tool ROI centerline indicator 742. Other exemplary parameter indicators shown in FIG. 7C include the arc tool ROI interior radius 750I and exterior radius 750E, scan direction arrows 770, a selector location indicator 785, and a rising/falling indicator 760. In exemplary embodiments, these other parameter indicators may be automatically linked and dynamically adjusted based on the cursor position, without requiring the user to depress and/or hold down a mouse button, similarly to the analogous elements of the circle tool 500. In the example shown in FIG. 7C, the user has continued to move the cursor 735 to a point down from the placed point 3, and the location of the ROI diameter 550E, the radial dimension of the arc tool ROI 750, the selector location indicator 785, and the scan direction arrows 770, have been dynamically adjusted accordingly, similarly to the analogous elements of the circle tool 500.

Figure 7D:
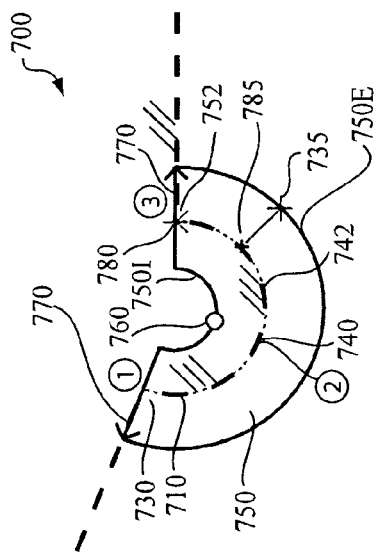

As shown in FIG. 7D, the user has continued to move the cursor 735 and places a point 4 at the location 790, and the automatically linked radial dimension of the arc tool ROI 750, selector location indicator 785, and scan direction arrows 770, have been dynamically adjusted accordingly. The location of the selector location indicator 785 now coincides with a desired prototypical scan location on the edge feature 710, and the scan direction arrow 770 is oriented along the desired radial direction. When the user places point 4 at the location 790, various parameter indicators are anchored and/or fixed based on the position of the placed point 4, and any previously undetermined tool parameters associated with the final set of parameter indicators are determined and used such that the tool may be run to automatically teach or train the tool. After the tool is trained, the rising/falling indicator 760 may be automatically filled with dark and light regions as shown in FIG. 7D, reflecting the direction of the dark-to-light transition that was determined by the tool operations during training. Subsequently, a series of edge points that are detected along the edge feature 710 based on the trained parameters may be marked on the display, for example using the known methods employed in commercially available machine vision systems. The user may then accept the training results and continue to other operations, or reject the training results, further modify the tool parameters, and retrain the tool until satisfactory results are achieved.

Figures 8A, 8B, 8C:
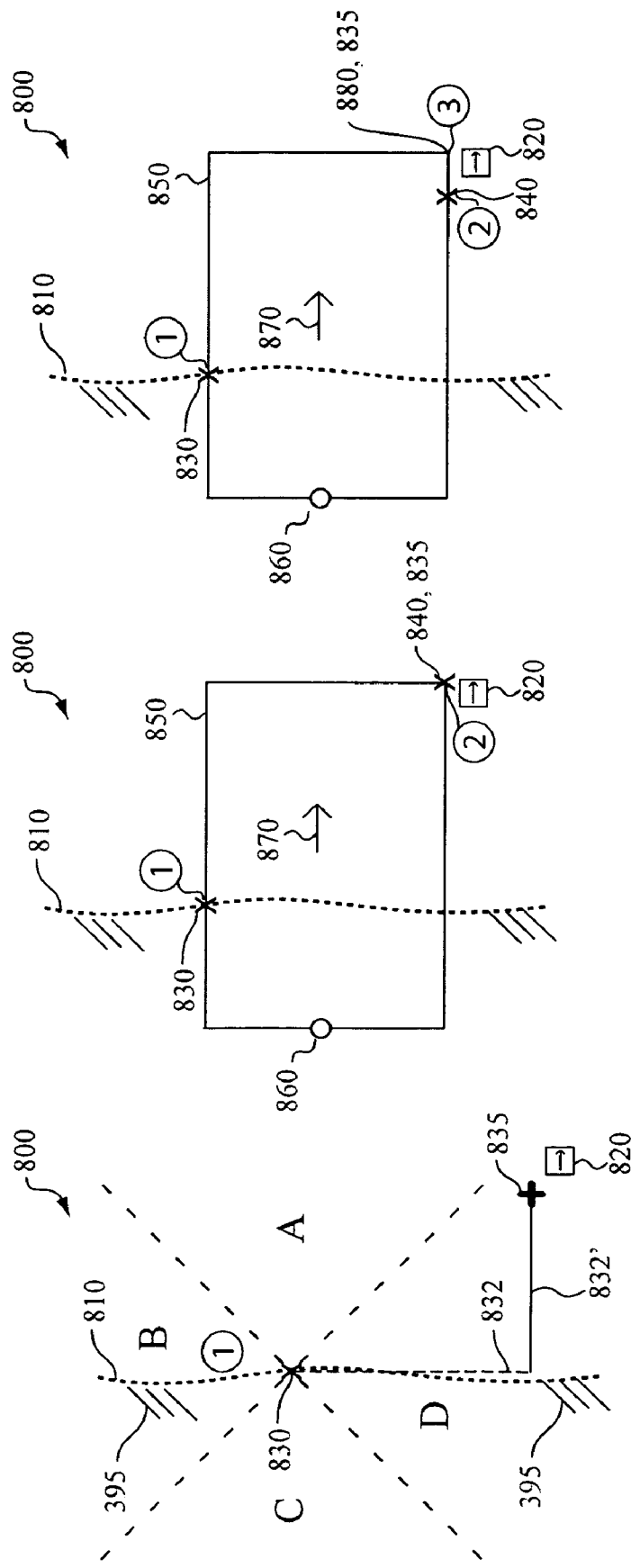
FIGS. 8A-8C are diagrams illustrating the operation of an exemplary edge auto focus tool on an edge feature.

FIGS. 8A-8C are diagrams illustrating the operation of an edge auto focus tool 800 on an edge feature 810. In operation, in a tool mode referred to as "multi-click-plus" herein, when the edge auto focus tool icon on a video tool bar is selected, as described below with reference to FIG. 11, an edge auto focus tool indicator 820, as shown in FIG. 8A, may appear on the display. The edge auto focus tool indicator 820 may be associated with a cursor point, as previously described with reference to the box tool indicator 320. In the example shown in FIG. 8A, the user initially places a point 1 along the edge feature 810 at a desired position 830, which indicates that the edge feature 810 is the target that should be used for the auto focus operations, and also bounds one end of a dimension of the auto focus tool ROI box 850 (shown in FIGS. 8B and 8C.) In the example shown in FIGS. 8A-8C, the point 1 bounds one end of the ROI "height" (or longitudinal dimension), while in other embodiments or examples, the point 1 may bound one end of the ROI "width" (which may still be regarded as the longitudinal dimension of the ROI), generally depending on the orientation on the edge feature 810 and the corresponding orientation of the edge auto focus tool 800. After placing the point 1, a parameter indicator, such as a crosshair, may be anchored at the point 1, and the user may then continue to move the cursor 835, which may be connected to the parameter indicator anchored at point 1 (at position 830) by a dotted construction line 832 and an orthogonal solid construction line 832', that may dynamically follow the cursor 835. The moving end of the construction line 832 and/or the orthogonal solid construction line 832', may be regarded as a parameter indicator that is automatically linked to be dynamically adjusted based on the cursor position. In exemplary embodiments, these parameter indicators may be dynamically adjusted to follow the cursor position without requiring the user to depress and/or hold down a mouse button. In operation, it is desirable for the user to approximately align the dotted construction line 832 (horizontally or vertically) with the edge feature 810.

As shown in FIG. 8A, the user has moved the cursor 835 to a second point below and to the right of the point 1, which tentatively bounds the other end of the dimension of the auto focus tool ROI box 850 that is bounded by point 1. Also shown in FIG. 8A are four quadrants A, B, C, and D, depicted relative to the point 1, which play a role in an operation outlined below. The four quadrants need not be displayed to the user.

Continuing, as shown in FIG. 8B, the user places a point 2 at a position 840. Placing the point 2 may anchor the other end of the dimension of the auto focus tool ROI box 850 that is bounded by point 1, may optionally cause an associated parameter indicator to appear at point 2, and may cause other parameter indicators of the auto focus tool 800, such as the entire ROI box 850, to appear. In the example shown in FIG. 8B, after placing point 2, the left side and the upper side of the ROI box 850 are anchored, and the right side and the bottom side of the ROI box 850 are automatically linked to be dynamically adjusted based on the position of the cursor 835, without requiring the user to depress and/or hold down a mouse button after placing point 2. After placing point 2, the user may continue to move the cursor 835. Other exemplary parameter indicators shown in FIG. 8B include the auto focus tool ROI box 850, a scan direction arrow 870, and a rising/falling indicator 860. The scan direction may be determined based on which of the four quadrants A, B, C, and D the point 2 falls in, for example, from left to right in quadrant D, from down to up in quadrant A, from right to left in quadrant B, and from up to down in quadrant C.

Continuing, as shown in FIG. 8C, the user places a point 3 at a position 880 and the width dimension of the auto focus tool ROI is dynamically adjusted, and anchored, accordingly. Placing the point 3 may anchor the entire auto focus tool ROI box 850. In the example shown in FIGS. 8B and 8C, the left end of the ROI width dimension is located at a default distance away from the dashed construction line 832 that is based on the distance of the point 2 from the dashed construction line 832. The right end of the ROI width dimension is then determined by the point 3. However, in other embodiments, the width dimension may simply be located symmetrically around the location of the dashed construction line 832, based on the location of the point 3. When the user places point 3 at the location 880, various parameter indicators are anchored and/or fixed based on the position of the placed point 3, and any previously undetermined tool parameters associated with the final set of parameter indicators are determined and used such that the tool may be run to automatically teach or train the tool. After the tool is trained, the rising/ falling indicator 860 may be left blank, indicating that the rising/falling parameter is not an essential tool parameter for the edge auto focus tool 800. However, if desired, the rising/falling parameter may be set by a user subsequently editing the tool, in a related menu or window of the edge auto focus tool user interface. In such a case, the rising/falling indicator 860 may be filled in accordingly, to indicate the rising/falling parameter is now set, and will be used. Subsequently, an autofocus operation may be performed based on the trained parameters using the known methods employed in commercially available machine vision systems. The user may then accept the training results and continue to other operations, or reject the training results, further modify the tool parameters, and retrain the tool until satisfactory results are achieved.

Figure 9C:
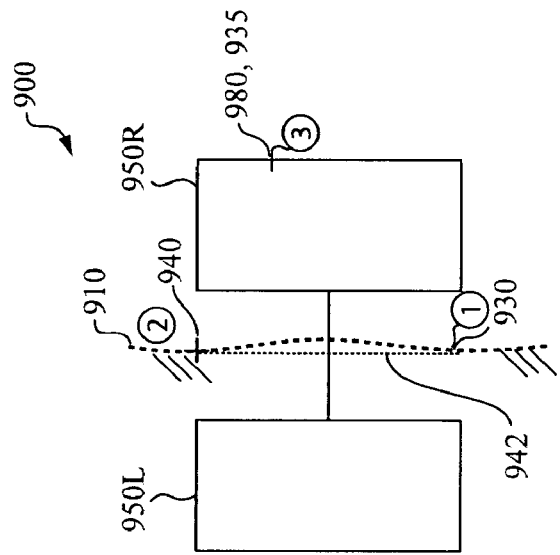
FIGS. 9A-9C are diagrams illustrating the operation of an exemplary dual area contrast tool on an edge feature.
Figure 9B:
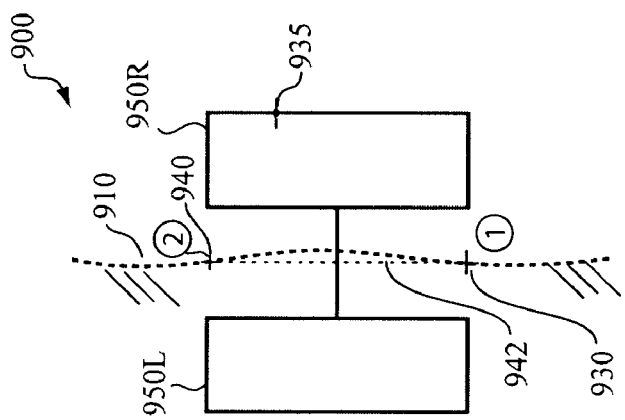
Figure 9A:
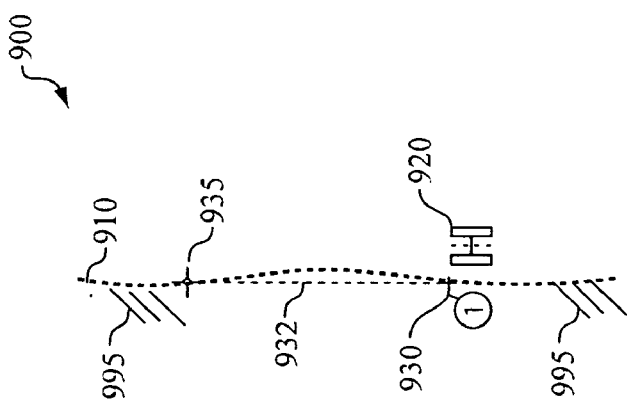

FIGS. 9A-9C are diagrams illustrating the operation of a dual area contrast (DAC) tool 900 around an edge feature 910. Teachings related to the purpose and general functions underlying the DAC tool 900 are disclosed in U.S. Pat. No. 6,542,180 to Wasserman and Tessadro (the '180 patent), which is incorporated herein by reference in its entirety. In operation, in a tool mode referred to as "multi-click-plus" herein, when the DAC tool icon on a video tool bar is selected, as described below with reference to FIG. 11, a DAC tool indicator 920, as shown in FIG. 9A, may appear on the display. The DAC tool indicator 920 may be associated with a cursor point, as previously described with reference to the box tool indicator 320. In the example shown in FIG. 9A, the user initially places a point 1 along the edge feature 910 at a desired position 930, which indicates that the DAC tool ROI's 950L and 950R (shown in FIGS. 9B and 9C) should be distributed about the edge feature 910, and also bounds one end of a longitudinal dimension (along the vertical direction in this case) of the DAC tool ROI's 950L and 950R. After placing the point 1, a parameter indicator, such as a crosshair, may be anchored at the point 1, and the user may then continue to move the cursor 935, which may be connected to the parameter indicator anchored at point 1 (at position 930) by a dotted construction line 932, that may follow the cursor 935 like a taut elastic band. The moving end of the construction line 932, may be regarded as a parameter indicator that is automatically linked to be dynamically adjusted based on the cursor position. In exemplary embodiments, the construction line 932 may follow the cursor position without requiring the user to depress and/or hold down a mouse button. In operation, it is desirable for the user to approximately align the dotted construction line 932 with the edge feature 910. As shown in FIG. 9A, the user has moved the cursor 935 to a second point along the edge feature 910, above the point 1, which tentatively bounds the second end of the longitudinal dimension of the DAC tool ROI's 950L and 950R.

Continuing, as shown in FIG. 9B, the user places a point 2 at a position 940. Placing the point 2 may anchor the second end of the height (or longitudinal) dimension of the DAC tool ROI's 950L and 950R, the location of the centerline indicator 942, may optionally cause an associated parameter indicator to appear at point 2, and may cause other parameter indicators of the DAC tool 900 to appear. In the example shown in FIG. 9B, after placing point 2, the location of the upper sides and the lower sides of the DAC tool ROI's 950L and 950R are anchored, and the lateral dimensions of the DAC tool ROI's 950L and 950R, are automatically linked to be dynamically adjusted based on the position of the cursor 935, without requiring the user to depress and/or hold down a mouse button after placing point 2. After placing point 2, the user may continue to move the cursor 935.

Continuing, as shown in FIG. 9C, the user places a point 3 at a position 980 and the lateral dimensions of the DAC tool ROI's 950L and 950R (their individual widths and lateral locations) are dynamically adjusted, and anchored, accordingly. In the example shown in FIGS. 9B and 9C, the lateral distance of the "interior limits" of the ROI's 950L and 950R from the centerline indicator 942 is a symmetrical default distance. The lateral distance of the "exterior limits" of the ROI's 950L and 950R from the centerline indicator 942 is a symmetrical distance that corresponds to the location of the point 3. However, in other embodiments, the lateral distance from the "interior limits" of the ROI's 950L and 950R from the centerline indicator 942 may simply be a proportion of the distance from the exterior limits to the centerline indicator 942.

When the user places point 3 at the location 980, various parameter indicators are anchored and/or fixed based on the position of the placed point 3, and any previously undetermined tool parameters associated with the final set of parameter indicators are determined and used such that the tool may be run to automatically teach or train the tool. Subsequently, a light-adjusting operation may be performed based on the results of the trained DAC tool 900, according to known methods employed in commercially available machine vision systems and/or as described in the '180 patent. The user may then accept the lighting results and the DAC tool 900 training results and continue to other operations, or reject the training results, further modify the tool parameters, and retrain the tool until satisfactory results are achieved.

Figure 10A:
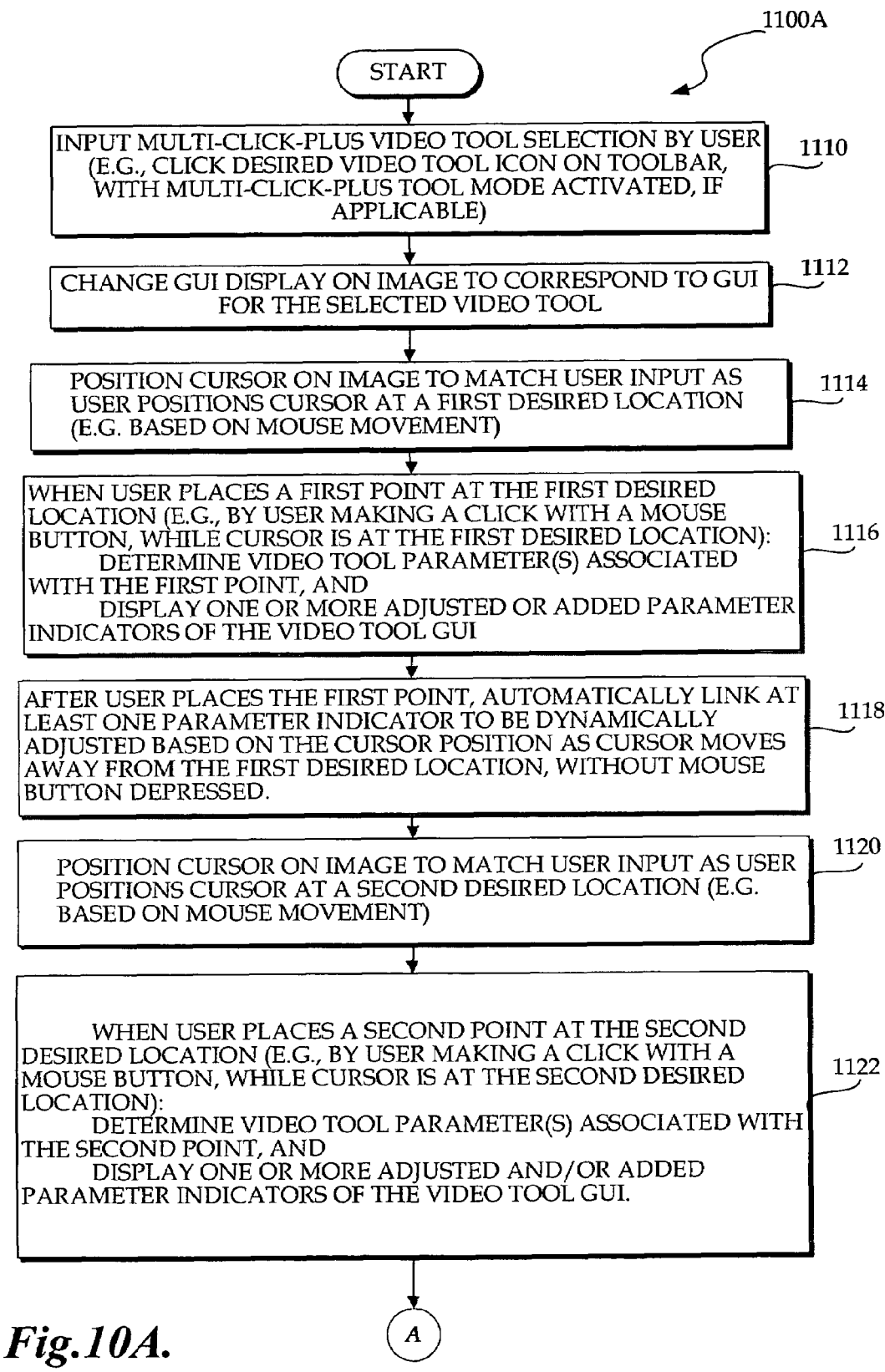
FIGS. 10A and 10B are flow diagrams illustrative of one embodiment of a routine for operation of a multi-click-plus video tool.
Figure 10B:
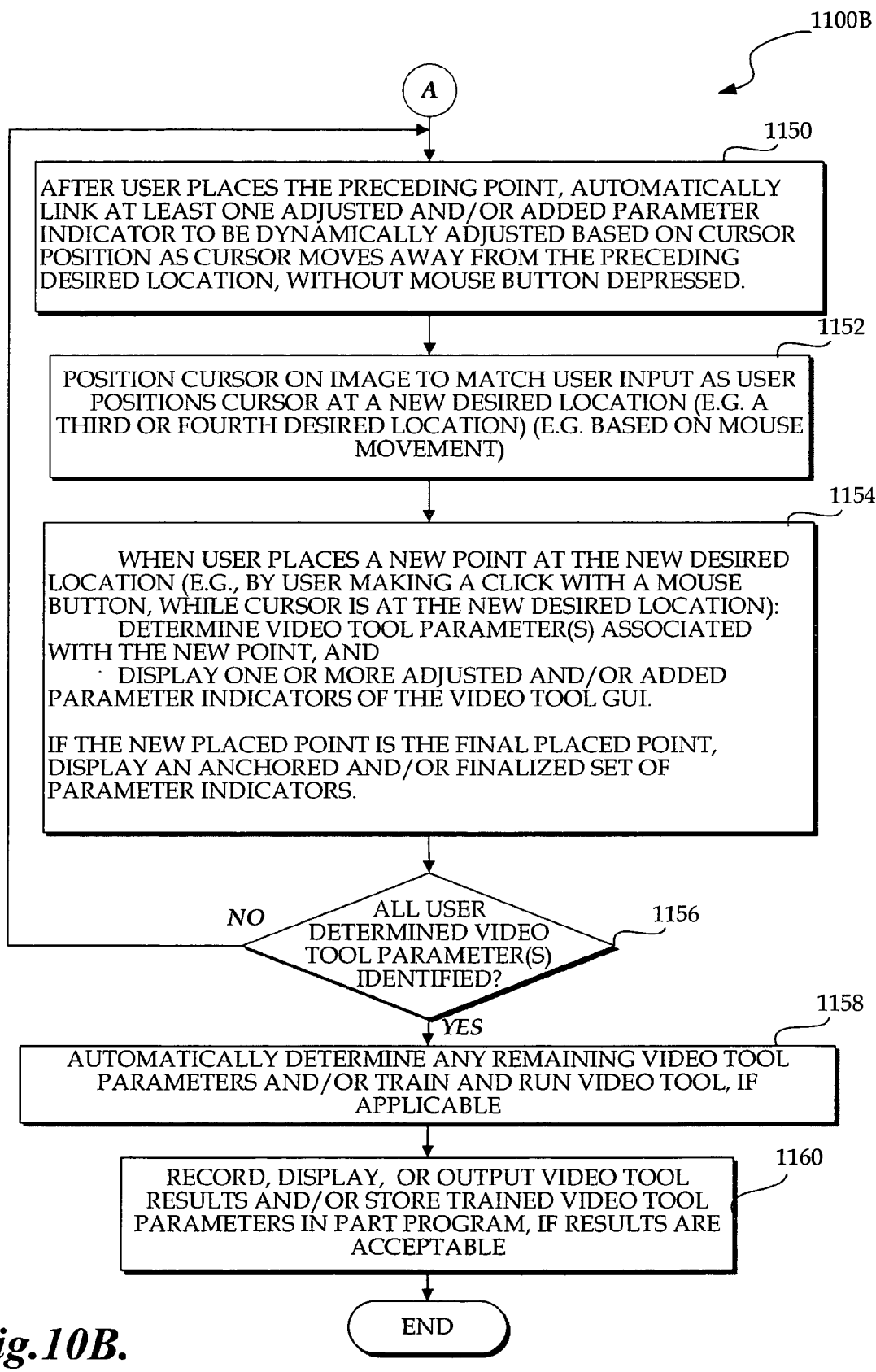

FIGS. 10A and 10B are flow diagrams illustrative of one exemplary embodiment of a routine 1100 for operation of a multi-click-plus video tool. As shown in FIG. 10A, at a block 1110, a multi-click-plus video tool selection is input by a user (e.g., the user may click a desired video tool icon on a toolbar, with the multi-click-plus tool mode activated, if applicable). At block 1112, the GUI display on the workpiece image is changed to correspond to the GUI for the selected video tool. At a block 1114, the cursor is positioned to match a user input as the user positions the cursor on the image at a first desired location (e.g., based on mouse movement).

At a block 1116, when the user places a first point at the first desired location (e.g., by the user making a click with a mouse button, while the cursor is at the first desired location), the video tool parameters associated with the first point are determined. In addition, one or more adjusted or added parameter indicators of the video tool GUI, corresponding to the entry of the first point, are displayed. One or more of the parameter indicators may be anchored.

At a block 1118, after the user places the first point, one or more parameter indicators may be automatically linked to be dynamically adjusted based on the cursor position (e.g., as the cursor moves away from the first point.) In various embodiments, one or more of the automatically linked parameter indicators may be dynamically adjusted based on the cursor position without requiring the user to depress and/or hold down a mouse button after placing the first point. At a block 1120, the cursor is positioned to match a user input as the user positions the cursor on the image at a second desired location (e.g., based on mouse movement).

At a block 1122, when the user places a second point at the second desired location (e.g., by the user making a click with a mouse button, while the cursor is at the second desired location), the video tool parameters associated with the second point are determined. In addition, one or more adjusted or added parameter indicators of the video tool GUI, corresponding to the entry of the second point, are displayed. One or more of the of the parameter indicators may be anchored.

As shown in FIG. 10B, from a point A the routine continues to a block 1150. At block 1150, after the user places the preceding point (e.g., the second point or a new point), one or more of the adjusted or added parameter indicators may be automatically linked to be dynamically adjusted based on the cursor position (e.g., as the cursor moves away from the second or new point.) In various embodiments, one or more of the automatically linked parameter indicators may be dynamically adjusted based on the cursor position without requiring the user to depress and/or hold down a mouse button after placing the second point. For example, when the multi-click-plus video tool is an edge-finding box tool, the first time that step 1150 is reached, after a second point is placed, a plurality of parameter indicators are may be automatically linked to be dynamically adjusted based on the cursor position. The plurality may include an edge "selector" location indicator, and an ROI dimension (or coordinate) indicator. A scan direction indicator may also be linked to be dynamically adjusted based on the cursor position.

At a block 1152, the cursor is positioned to match a user input as the user positions the cursor on the image at a new desired location (e.g., a third or fourth desired location.) At a block 1154, when the user places a new point at the new desired location (e.g., by the user making a click with a mouse button, while the cursor is at the new desired location), the video tool parameters associated with the new point are determined. In addition, one or more adjusted or added parameter indicators of the video tool GUI, corresponding to the entry of the new point, may be displayed. One or more of the of the parameter indicators may be anchored. If the new placed point is the final placed point required for determining the video tool parameters, an anchored and/or finalized set of video tool parameter indicators may be displayed.

At a decision block 1156, a determination is made as to whether all of the user-determined video tool parameters have been identified. If all of the user-determined tool parameters have not yet been identified, then the routine returns to block 1150, to perform operations for identifying additional tool parameters. For example, when the multi-click-plus video tool is an edge-finding arc or circle tool, the second time that step 1150 is reached, after a third point has been placed, a plurality of parameter indicators are may be automatically linked to be dynamically adjusted based on the cursor position. The plurality may include an edge "selector" location indicator, and an ROI dimension (or coordinate) indicator. A scan direction indicator may also be linked to be dynamically adjusted based on the cursor position. Otherwise, if all of the user-determined tool parameters have been identified, then the routine continues to a block 1158. At a block 1158, any remaining video tool parameters are automatically determined, and/or the video tool may be trained and/or run based on all the determined parameters. At a block 1160, the results of running the trained video tool are recorded, displayed or output (e.g., during manual or learn mode operations) and/or if the results are acceptable, the determined and trained video tool parameters may be recorded or stored in a part program (e.g., during learn mode operations, if accepted by a user.)

Figure 11:
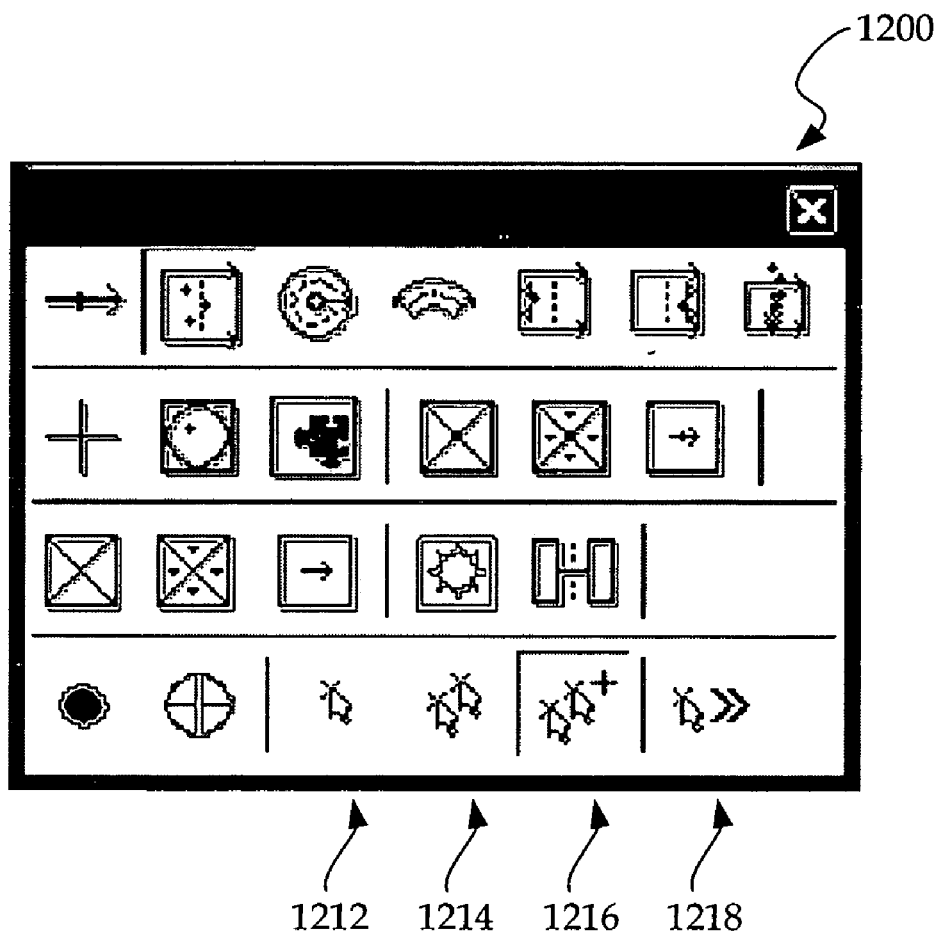
FIG. 11 is a diagram illustrating a toolbar from which various video tools and video tools modes may be selected.

FIG. 11 is a diagram illustrating a video toolbar 1200 from which various video tools and modes may be selected. As shown in FIG. 11, the toolbar 1200 includes selections for numerous video tools, including those described above with respect to FIGS. 3-10. The toolbar 1200 also includes selectors for various modes, including a selector 1212 for a known single click mode, a selector 1214 for a multi-click mode, a selector 1216 for a multi-click-plus mode. In operation, in one embodiment, after the user selects a selector it determines the active tool mode, and may stay highlighted to indicate the active tool mode, as exemplified by the multi-click-plus selector 1216 shown in FIG. 11. Thereafter, when one of the individual video tools is selected, it will operate according to the selected active mode. The selector 1218 is for a known "auto run" mode, that may be activated in conjunction with other modes. In auto run mode, when the final user-determined video tool data is entered, the video tool automatically runs and trains itself without waiting for a further action or instruction from the user.

FIGS. 12A and 12B are diagrams of a chart 1400 that illustrates one set of exemplary embodiments of how the determination of various video tool parameters may correspond to a sequence of point placements, which may be designated "clicks" (e.g., of a button of a mouse, trackball, or other user data entry device). In the chart 1400, "MC+" stands for multi-click-plus tool operations (e.g., in a multi-click-plus tool mode) and "MC" stands for multi-click tool operations (e.g., in a multi-click tool mode) described further below. Exemplary MC+ operations for a number of video tools have been described above with respect to FIGS. 3-10, therefore the rows 1410, 1420, 1430, 1460, and 1470 are not described in detail, but will be understood based on previous descriptions and general teachings. For purposes of clarification, the entries of row 1410 will be explained.

As shown in FIG. 12A, in row 1410, the first column indicates that the operations of a multi-click-plus Box tool and/or a multi-click-plus Autotrace tool are summarized in row 1410. Continuing across row 1410, column A indicates that when operating the respective video tool GUI's of the subject tools, the first click establishes the ROI height end point #1. Column B indicates that a second click establishes the other end point of the ROI height, end point #2, and column C indicates that the second click establishes the ROI angular orientation, as well. Column D indicates that a third click establishes the ROI width (symmetric about the midline), and columns E and F, respectively, indicate that the third click establishes the selector location, and the scan direction, as well. Column G indicates that sampling direction is determined to follow a direction from the location of point #1, established by the first click, toward the location of point #2, established by the second click The remainder of the rows in FIGS. 12A and 12B may be understood based on the preceding explanation. A comparison of each respective row describing "MC tools" with the corresponding "MC+ tool" row above it (corresponding to similar video tools, operated in different modes), shows that the MC tools operate similar to the MC+ tools, with the exception that each of the parameters associated with the operations of columns D, E, F, and G, are set "by default", that is, the user is only required to perform the clicks indicated in columns A, B and C, in order to completely define the parameters of the MC tools. Accordingly, the MC tool mode has the advantage of offering simpler and more convenient tool operation than the MC+ mode, but it has the disadvantage that the default tool parameters are not customized to a particular feature. Therefore, the MC tool mode may not be suitable for performing inspection operations for some features, for example, some features similar to those shown in FIGS. 4 and 6. Nevertheless, in some embodiments, an MC tool may include operating advantages similar to those provided in some embodiments of the MC+ tools. For example, in some embodiments it is advantageous that after a user places a point, one or more parameter indicators may be automatically linked to be dynamically adjusted based on the cursor position (e.g., as the cursor moves away from the point), and that they may be dynamically adjusted based on the cursor position without requiring the user to depress and/or hold down a mouse button after placing the point.

While exemplary sequences of operations have been outlined when describing various exemplary embodiments of multi-click-plus video tools with reference to FIGS. 3-11, it will be appreciated that in other exemplary embodiments certain operations may be performed in other sequences and/or one or more of the described operating features or GUI features may be omitted, and the other inventive aspects of the methods and GUI's disclosed herein may still provide substantial benefits. Thus, while the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for operating a video tool to determine video tool parameters used by the video tool, wherein:
    the video tool comprises video tool operations performed to analyze features in a workpiece image, the video tool operations comprise at least one image analysis operation, and at least some of the video tool operations are controlled based on the video tool parameters;
    the video tool further comprises a video tool graphical user interface (GUI) including a plurality of displayable parameter indicators corresponding to video tool parameters, wherein at least some of the parameter indicators may be added to modify a display of the video tool GUI, and at least some of the parameter indicators may be adjusted in the display of the video tool GUI, and at least some of the parameter indicators may be anchored in the display of the video tool GUI; and
    the video tool is included in a machine vision inspection system, the machine vision inspection system comprising a camera portion usable to provide the workpiece image, a control system portion that includes the video tool, and a display portion usable to display the workpiece image and the video tool GUI overlaying the workpiece image,
    the method comprising:
    (a) displaying the video tool GUI and a cursor overlaying a workpiece image after a user selects the video tool, wherein the user may position the cursor at a desired position;
    (b) determining a plurality of video tool parameters that are controlled by the user placing a plurality of respective placed points at respective desired positions while the video tool GUI is displayed, and
    (c) for at least one respective time when the user places a respective placed point, performing video tool operations comprising automatically linking and displaying at least one newly-linked parameter indicator that is dynamically adjusted based on the cursor position as the cursor is moved away from that respective placed point.

2. The method of claim 1, wherein, in step (c), automatically linking and displaying at least one newly-linked parameter indicator that is dynamically adjusted comprises automatically linking and displaying a plurality of newly-linked parameter indicators that are dynamically adjusted.

3. The method of claim 2, wherein the plurality of newly-linked parameter indicators that are dynamically adjusted comprises at least two parameter indicators from a group comprising: a first region of interest parameter indicator, a second region of interest parameter indicator, an edge selector location indicator, and a scan direction indicator.

4. The method of claim 3, wherein the plurality of newly-linked parameter indicators that are dynamically adjusted comprises at least the first region of interest parameter indicator, the edge selector location indicator, and the scan direction indicator.

5. The method of claim 1, wherein, in step (b), the user placing a plurality of respective placed points comprises the user placing each respective placed point using the same point-placing operation.

6. The method of claim 5, wherein the point placing operation comprises one of a) the user depressing a button of a user input device, and b) the user rapidly depressing and releasing a button of a user input device.

7. The method of claim 1, wherein, in step (c), the video tool operations further comprise anchoring and displaying at least one newly-anchored parameter indicator at that respective placed point.

8. The method of claim 7, wherein the video tool is one of a box tool, a circle tool, an arc tool, and auto-trace tool, and a dual area contrast tool, and when the user places a first respective placed point, the operations of step (c) are performed, wherein the at least one newly-anchored parameter indicator comprises the first end of a construction line, the first end anchored and displayed at the first respective placed point, and the at least one newly-linked parameter indicator that is dynamically adjusted comprises a portion of the construction line other than the first end.

9. The method of claim 8, wherein the video tool is one of a box tool, an auto-trace tool, and a dual area contrast tool, and when the user places a second respective placed point, the method further comprises anchoring and displaying a centerline indicator at the location of the construction line.

10. The method of claim 8, wherein the video tool is one of a circle tool and an arc tool, and when the user places a second respective placed point, the construction line is dynamically adjusted to form a curved construction line based on the first respective placed point, the second respective placed point, and the position of the cursor as the cursor is moved away from the second respective placed point, and when the user places a third respective placed point, the method further comprises anchoring and displaying a centerline indicator at the location of the construction line.

11. The method of claim 7, wherein, in step (b), the user placing a plurality of respective placed points comprises the user placing three respective placed points, and
    when the user places a first respective placed point, the operations of step (c) are performed a first time corresponding to the first respective placed point; and
    when the user places a second respective placed point, the operations of step (c) are performed a second time, wherein the second time operating the video tool to automatically link and display at least one newly-linked parameter indicator that is dynamically adjusted comprises operating the video tool to automatically link a plurality of newly-linked parameter indicators that are dynamically adjusted.

12. The method of claim 11, wherein the video tool is one of a box tool and an auto-trace tool, and when the user places the second respective placed point and the operations of step (c) are performed the second time, the at least one newly-anchored parameter indicator of the second time corresponds to a first dimension of a tool region of interest, and the plurality of newly-linked parameter indicators of the second time comprise at least two parameter indicators from a group comprising: a second dimension of the tool region of interest, an edge selector location indicator, and a sampling direction indicator.

13. The method of claim 7, wherein, in step (b), the user placing a plurality of respective placed points comprises the user placing four respective placed points, and
 when the user places a first respective placed point, the operations of step (c) are performed a first time corresponding to the first respective placed point; and
 when the user places a second respective placed point, the operations of step (c) are performed a second time corresponding to the second respective placed point; and
 when the user places a third respective placed point, the operations of step (c) are performed a third time, wherein the third time operating the video tool to automatically link and display at least one newly-linked parameter indicator that is dynamically adjusted comprises operating the video tool to automatically link a plurality of newly-linked parameter indicators that are dynamically adjusted.

14. The method of claim 13, wherein the video tool is one of a circle tool and an arc tool, and when the user places the third respective placed point and the operations of step (c) are performed the third time, the at least one newly-anchored parameter indicator of the third time corresponds to a first dimension of a tool region of interest, and the plurality of newly-linked parameter indicators of the third time comprise at least two parameter indicators from a group comprising: a radial dimension of the tool region of interest, an edge selector location indicator, and a sampling direction indicator.

15. The method of claim 1, wherein the user places a final respective placed point that is used to determine a final tool parameter related to a dimension of a region of interest of the video tool, and when the user does so, tool parameters related to an edge selector location and a scan direction are also determined based on the placement of the final respective placed point.

16. The method of claim 15, wherein when the user places the final respective placed point that is used to determine a final tool parameter related to a dimension of a region of interest of the video tool, all region of interest parameter indicators of the video tool are anchored, an edge selector location indicator is anchored based at least partially on the position of the final respective placed point, and a scan direction indicator is finalized based at least partially on the position of the final respective placed point.

17. The method of claim 1, wherein the video tool operates in a plurality of modes including a mode wherein the video tool operates according to the method, and in step (a) the user selects the video tool by selecting a tool mode selector corresponding to the method and a video tool selector corresponding to the video tool, in a video tool bar included in a user interface of the machine vision inspection system.

18. A method for operating a video tool to determine video tool parameters used by the video tool, wherein:
 the video tool comprises video tool operations performed to analyze features in a workpiece image, the video tool operations comprise at least one image analysis operation, and at least some of the video tool operations are controlled based on the video tool parameters;
 the video tool further comprises a video tool graphical user interface (GUI) including a plurality of displayable parameter indicators corresponding to video tool parameters, wherein at least some of the parameter indicators may be added to modify a display of the video tool GUI, and at least some of the parameter indicators may be adjusted in the display of the video tool GUI, and at least some of the parameter indicators may be anchored in the display of the video tool GUI; and
 the video tool is included in a machine vision inspection system, the machine vision inspection system comprising a camera portion usable to provide the workpiece image, a control system portion that includes the video tool, and a display portion usable to display the workpiece image and the video tool GUI overlaying the workpiece image,
 the method comprising:
  (a) displaying the video tool GUI and a cursor overlaying a workpiece image after a user selects the video tool, wherein the user may position the cursor at a desired position;
  (b) determining a plurality of video tool parameters that are controlled by the user placing a plurality of respective placed points at respective desired positions while the video tool GUI is displayed; and
  (c) modifying the parameter indicators displayed in the video tool GUI at respective times based on the user placing the respective placed points,
 wherein:
  in step (b), the user placing a plurality of respective placed points comprises the user placing each respective placed point using the same point-placing operation;
  the video tool GUI includes the user placing a sequence of respective placed points; and
  before the user places a final respective placed point that is the last respective placed point in the sequence, a plurality of different types of parameter indicators are linked to be dynamically adjusted at the same time based on the position of the cursor.

19. The method of claim 18, wherein the user places a sequence of at most four respective placed points, and before the user places the final respective placed point that is the last respective placed point in the sequence, the plurality of different types of parameter indicators that are linked to be dynamically adjusted at the same time comprise at least two parameter indicators from a group comprising: a first region of interest parameter indicator, a second region of interest parameter indicator, an edge selector location indicator, and a scan direction indicator.

* * * * *

UNITED STATES PATENT AND TRADEMARK OFFICE
CERTIFICATE OF CORRECTION

PATENT NO. : 7,627,162 B2  Page 1 of 1
APPLICATION NO. : 11/185561
DATED : December 1, 2009
INVENTOR(S) : C. Blanford et al.

It is certified that error appears in the above-identified patent and that said Letters Patent is hereby corrected as shown below:

| COLUMN | LINE | ERROR |
|---|---|---|
| 22 | 17 | "and auto-trace tool," should read |
| (Claim 8, | line 2) | --an auto-trace tool,-- |

Signed and Sealed this

First Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,627,162 B2
APPLICATION NO. : 11/185561
DATED : December 1, 2009
INVENTOR(S) : Blanford et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1137 days.

Signed and Sealed this

Second Day of November, 2010

David J. Kappos
*Director of the United States Patent and Trademark Office*